United States Patent
Ohtsubo et al.

(10) Patent No.: US 7,041,452 B2
(45) Date of Patent: May 9, 2006

(54) METHOD OF DETECTING THE PRESENCE OF ABSENCE OF MIXED VARIETIES IN GRAINS, AND IDENTIFYING THE MIXED VARIETIES

(75) Inventors: Kenichi Ohtsubo, Inashiki-gun (JP); Sumiko Nakamura, Inashiki-gun (JP); Tsuyoshi Miyamura, Otsu (JP); Satoshi Kumo, Otsu (JP); Ikunoshin Kato, Otsu (JP)

(73) Assignees: National Food Research Institute, Tsukuba (JP); Takara Bio Inc., Otsu (JP)

( * ) Notice: Subject to any disclaimer, the term of this patent is extended or adjusted under 35 U.S.C. 154(b) by 327 days.

(21) Appl. No.: 10/217,106

(22) Filed: Aug. 13, 2002

(65) Prior Publication Data
US 2003/0138806 A1    Jul. 24, 2003

(30) Foreign Application Priority Data
Aug. 21, 2001   (JP) .............................. 2001-250308

(51) Int. Cl.
*C12Q 1/68*   (2006.01)
*C12P 19/34*   (2006.01)
*C07H 21/02*   (2006.01)
*C07H 21/04*   (2006.01)

(52) U.S. Cl. ................... 435/6; 435/91.1; 435/91.2; 536/23.1; 536/23.6; 536/24.3; 536/24.33

(58) Field of Classification Search .................... None
See application file for complete search history.

(56) References Cited

OTHER PUBLICATIONS

U.S. Appl. No. 10/237,016, filed Sep. 9, 2002, Ohtsubo et al.

*Primary Examiner*—Carla J. Myers
(74) *Attorney, Agent, or Firm*—Oblon, Spivak, McClelland, Maier & Neustadt, P.C.

(57) ABSTRACT

Provided is a DNA-level grain variety discrimination method of detecting the presence or absence of any other varieties of grains in object grains of a certain variety through multiplex PCR that uses the DNAs extracted from the grains or from their processed products as templates. The method is characterized in that the multiplex PCR uses pair primer groups that are for discriminative detection of negative bands not appearing in the band pattern of the object variety but selectively appearing only in the band patterns of the other mixed varieties. The method has made it possible to rapidly and simply detect the presence or absence of mixed varieties in high-quality grains such as "Koshihikari", and to identify the mixed varieties.

42 Claims, 4 Drawing Sheets

US 7,041,452 B2

METHOD OF DETECTING THE PRESENCE OF ABSENCE OF MIXED VARIETIES IN GRAINS, AND IDENTIFYING THE MIXED VARIETIES

FIELD OF THE INVENTION

The present invention relates to a method of detecting the presence or absence of mixed varieties in grains, and identifying the mixed varieties. For example, it relates to a DNA-level grain variety discrimination method of detecting the presence or absence of mixed different rice in tasty high-quality rice, and identifying the varieties of the mixed rice therein. More precisely, the invention relates to a method of detecting the presence or absence of mixed different varieties in grains by analyzing the DNAs extracted from grains such as rice, wheat, corn or barley or from their processed products through multiplex PCR of using the DNAs as templates in the presence of suitable pair primers to thereby identify the mixed varieties from the band patterns of the amplified DNAs.

BACKGROUND OF THE INVENTION

In general, the price of grains is determined depending on the processability and the palatability of grains, and the price of grains of better quality is higher. For rice, for example, palatable rice of typically "Koshihikari", "Hitomebore", "Hinohikari" and "Akitakomachi" that are the best four varieties of rice harvested in 2000 in Japan is more accepted by consumers who need palatable rice, and the prices of these varieties of rice are high.

However, different rice is mixed into such high-quality rice by some dishonest traders, and the unfair mixed rice with a false indication is sold on the market. This is a matter of grave concern. Under the revised JAS Act that is in force from April 2001, rice traders have an obligation to express the variety of rice, the rice-producing district and the rice harvest year on all rice packages to be on the market. Given that situation, it is necessary to develop a technique of scientifically inspecting whether the indication given on rice packages fairly corresponds to the contents of the packages.

Heretofore, varieties of grains such as rice have been distinguished by the plant morphology, the grain morphology and the enzyme polymorphism in leaves and grains. At present, however, a variety of "Koshihikari" and its related varieties account for more than 70% of the overall rice yield in Japan, and this means that the rice production in Japan is mostly shared by such closely related varieties. In that situation, it is impossible to detect the presence or absence of any different variety mixed in a certain variety of rice according to the conventional method as above.

We, the present inventors have previously developed some techniques of rice variety discrimination through RAPD method or through a method of using STS primers, and have disclosed them in the *Journal of the Food Science and Technology of Japan*, Vol. 46, No. 3, pp. 117–122; Japanese Patent No. 3,048,149; and Japanese Patent Laid-Open No. 2001-95589.

These techniques make it possible to discriminate clearly a certain variety of rice from another variety that differs from it. However, when the discrimination band pattern of a different variety of rice to be discriminated from "Koshihikari" partly overlaps with that of "Koshihikari", or when about 10 to 30% of a different variety of rice that gives a smaller number of discrimination bands than "Koshihikari" is mixed with "Koshihikari", or when different several varieties of rice are mixed, it is difficult to individually detect and identify those different varieties of the mixed rice.

In checking a rice sample whether it contains mixed rice by the use of three or four types of primer sets, even when no DNA band specific to mixed rice has appeared in the band pattern of the sample, the probability that the sample is just the intended variety of high-quality rice only is, at present, at most 88 to 94% ($=1-(0.5)^3$ to $^4$) and is not high enough.

In addition, when some bands specific to mixed rice have appeared in the DNA band pattern, the varieties of the mixed rice need to be identified in most cases. Therefore, the detection of only the discrimination bands that should not appear in the band pattern of the object variety of rice is insufficient for the information to identify the varieties of mixed rice, and further PCR is needed for individually identifying the varieties of mixed rice.

According to the conventional techniques heretofore known in the art, it is impossible to rapidly and accurately detect the presence or absence of mixed varieties in grains and to individually identify the mixed varieties in a simplified manner.

SUMMARY OF THE INVENTION

The present invention is to provide a simplified method of rapidly and accurately detecting the presence or absence of any other mixed varieties in high-quality grains such as "Koshihikari" and identifying the mixed varieties.

We, the present inventors have assiduously studied to attain the object as above, and, as a result, have found that, when DNAs extracted from a grain sample are subjected to specific multiplex PCR amplification using them as templates, it is possible to rapidly and accurately detect the presence or absence of mixed varieties in the grain sample and to individually identify the mixed varieties in a simplified manner. The multiplex PCR amplification of the extracted DNAs comprises primary multiplex PCR with pair primer groups that are for discriminative detection of negative bands not appearing in the band pattern of the objective high-quality variety but appearing only in the band patterns of different varieties specifically thereto, optionally combined with secondary multiplex PCR with selective pair primers specific to the expressed band patterns to thereby identify the polymorphism of the amplified DNA. The method makes it possible to confirm that the grain sample is of the object variety and to confirm whether any mixed varieties are present or absent in the sample, and further makes it possible to rapidly and accurately identify the mixed varieties in the sample in a simplified manner. On the basis of these findings, we have completed the present invention.

Specifically, the invention provides a DNA-level grain variety discrimination method of detecting the presence or absence of any other varieties of grains in object grains of a certain variety through multiplex PCR that uses the DNAs extracted from the grains or from their processed products as templates, which is characterized in that the multiplex PCR uses pair primer groups that are for discriminative detection of negative bands not appearing in the band pattern of the object variety but selectively appearing only in the band patterns of the other mixed varieties.

In one embodiment of the DNA-level grain variety discrimination method of the invention, when no discrimination band has appeared in the band pattern of multiplex PCR with the pair primer groups for negative band discrimination, the sample is further subjected to secondary multiplex PCR with pair primers selected from pair primer groups for discriminative detection of positive band appearing specific to only the object variety and/or pair primer groups for discriminative detection of negative band not appearing specific to only the object variety to thereby confirm that the sample is of the object variety by the expressed DNA band pattern.

The present invention also provides a kit used for the DNA-level grain variety discrimination method of the present invention. The kit contains pair primer groups that are for discriminative detection of negative bands not appearing in the band patterns of the object variety but selectively appearing only in the band patterns of the other mixed varieties. The kit which further contains pair primer groups for discriminative detection of positive band appearing specific to only the object variety and/or pair primer groups for discriminative detection of negative band not appearing specific to only the object variety by the expressed band pattern is preferably used for the present invention.

The pair primer groups mentioned above can be contained in the kit of the present invention. Furthermore, the kit may contain reagents for PCR, such as DNA polymerase, buffer for reaction, etc.

The DNA-level grain variety discrimination method of the invention is favorable to grains of rice, wheat, corn or barley. In its embodiment, the rice of the object variety is high-quality rice.

For example, the high-quality rice is any of "Koshihikari", "Hitomebore", "Akitakomachi" or "Hinohikari".

In another embodiment of the DNA-level grain variety discrimination method of the invention for high-quality rice, when some discrimination bands have appeared in the band patterns of multiplex PCR with the pair primer groups for negative band discrimination, the sample is further subjected to secondary multiplex PCR that uses, as a template, the DNA extracted from every one grain of the sample and uses pair primers selected from pair primer groups for discriminative detection of positive band appearing specific to only the object variety and/or pair primer groups for discriminative detection of negative band not appearing specific to only the object variety to thereby identify the mixed varieties by the expressed DNA band patterns.

In still another embodiment of the DNA-level grain variety discrimination method of the invention, the pair primers for the multiplex PCR are at least two primers selected from a group of pair primers each composed of from 13 to 29 bases and prepared by deleting 1 to 17 bases from the 3'-side of pair primers of A6F30 an A6R30; A7F30 an A7R30; A52F30 an A52R30; B1F30 B1R30; B7F30 and B7R30; B18F30 and B18R30; B43F30 and B43R30; D4F30 and D4R30; E22F30 and E22R30; E30F30 and E30R30; F6F 30 and F6R30; G4F30 and G4R30; G22F30 and G22R30; G28F30 and G28R30; J6F30 and J6R30; M2CGF30 and M2CGR30; M11F30 and M11R30; P3F30 and P3R30; P5F30 and P5R30; Q16F30 and Q16R30; S13F30and S13R30; T8F30 and T8R30; T16F30 and T16R30; WK9F30 and WK9R30, described in SEQ ID Nos. 1 and 2; 5 and 6; 9 and 10; 13 and 14; 17 and 18; 21 and 22; 25 and 26; 29 and 30; 33 and 34; 37 and 38; 41 and 42; 45 and 46; 49 and 50; 53 and 54; 57 and 58; 61 and 62; 65 and 66; 69 and 70; 73 and 74; 77 and 78; 81 and 82; 85 and 86; 89 and 90; 93 and 94, respectively, in Sequence Listing attached hereto.

In still another embodiment of the DNA-level grain variety discrimination method of the invention, the pair primers for the multiplex PCR are at least two primers selected from pair primer groups of A6F21 and A6R22; A7F19 and A7R16; A52F29 and A52R21; B1F25 and B1R20; B7F22 and B7R17; B18F15 and B18R21; B43F17 and B43R18; D4F23 and D4R24; E22F20 and E22R21; E30F28 and E30R24; F6F25 and F6R22; G4F18 and G4R24; G22F27 and G22R23; G28F17 and G28R28; J6F18 and J6R20; M2CGF16 and M2CGR15; M11F20 and M11R20; P3F20 and P3R15; P5F20 and P5R25; Q16F25 and Q16R20; S13F25 and S13R24; T8F22 and T8R25; T16F24 and T16R26; WK9F20 and WK9R20, described in SEQ ID Nos. 3 and 4; 7 and 8; 11 and 12; 15 and 16; 19 and 20; 23 and 24; 27 and 28; 31 and 32; 35 and 36; 39 and 40; 43 and 44; 47 and 48; 51 and 52; 55 and 56; 59 and 60; 63 and 64; 67 and 68; 71 and 72; 75 and 76; 79 and 80; 83 and 84; 87 and 88; 91 and 92; 95 and 96, respectively, in Sequence Listing attached hereto.

As used herein, the present inventors use a shorthand in which the discrimination band acronym is used to designate the primer pair from which the band arises via PCR amplification procedures. For sake of convenience and to serve as a reference, the present inventors provide the following description of the discrimination band designator and the primer pair giving rise thereto:

| Discrimination Band Acronym | Primer Pair (listed as forward, then reverse) |
| --- | --- |
| A6 | SEQ ID NOs: 3 and 4 |
| A7 | SEQ ID NOs: 7 and 8 |
| A52 | SEQ ID NOs: 11 and 12 |
| B1 | SEQ ID NOs: 15 and 16 |
| B7 | SEQ ID NOs: 19 and 20 |
| B18 | SEQ ID NOs: 23 and 24 |
| B43 | SEQ ID NOs: 27 and 28 |
| D4 | SEQ ID NOs: 31 and 32 |
| E22 | SEQ ID NOs: 35 and 36 |
| E30 | SEQ ID NOs: 39 and 40 |
| F6 | SEQ ID NOs: 43 and 44 |
| G4 | SEQ ID NOs: 47 and 48 |
| G22 | SEQ ID NOs: 51 and 52 |
| G28 | SEQ ID NOs: 55 and 56 |
| J6 | SEQ ID NOs: 59 and 60 |
| M2CG | SEQ ID NOs: 63 and 64 |
| M11 | SEQ ID NOs: 67 and 68 |
| P3 | SEQ ID NOs: 71 and 72 |
| P5 | SEQ ID NOs: 75 and 76 |
| Q16 | SEQ ID NOs: 79 and 80 |
| S13 | SEQ ID NOs: 83 and 84 |
| T8 | SEQ ID NOs: 87 and 88 |
| T16 | SEQ ID NOs: 91 and 92 |
| WK9 | SEQ ID NOs: 95 and 96 |

In still another embodiment of the DNA-level grain variety discrimination method of the invention, the high-quality rice is "Koshihikari", and the multiplex PCR uses a primer set of four pair primers, B43, G22, M11 and WK9, and/or a pair primer set for negative band discrimination of at least three pair primers selected from a group of A6, B7, E30, F6, G4, M2CG, S13, T8, T16 and WK9.

In still another embodiment of the DNA-level grain variety discrimination method of the invention, the high-quality rice is "Hitomebore", and the multiplex PCR uses a pair primer set for negative band discrimination of at least three pair primers selected from a group of A6, B7, F6, G4, P3, S13, T8 and T16, and/or a primer set of five pair primers, B7, G4, G22, P5 and WK9.

In still another embodiment of the DNA-level grain variety discrimination method of the invention, the high-quality rice is "Akitakomachi", and the multiplex PCR uses a pair primer set for negative band discrimination of at least three pair primers selected from a group of A6, B7, E30, F6, G4, G22, M2CG, P3, S13 and T16, and/or a primer set of four pair primers, A6, B7, M2CG and P3, or four pair primers, WK9, B43, M11 and G22.

In still another embodiment of the DNA-level grain variety discrimination method of the invention, the high-quality rice is "Hinohikari", and the multiplex PCR uses a pair primer set for negative band discrimination of at least three pair primers selected from a group of A6, B7, B43, E22, E30, F6, G4, G28, S13, T8 and T16, and/or a primer set of four primers, B43, F6, G28 and T16, or five pair primers, B43, G22, G28, P5 and WK9.

In still another embodiment of the DNA-level grain variety discrimination method of the invention, the sample rice is boiled rice.

In still another embodiment of the DNA-level grain variety discrimination method of the invention, every one grain of the sample rice is inspected one by one.

DETAILED DESCRIPTION OF THE INVENTION

Figure 1:
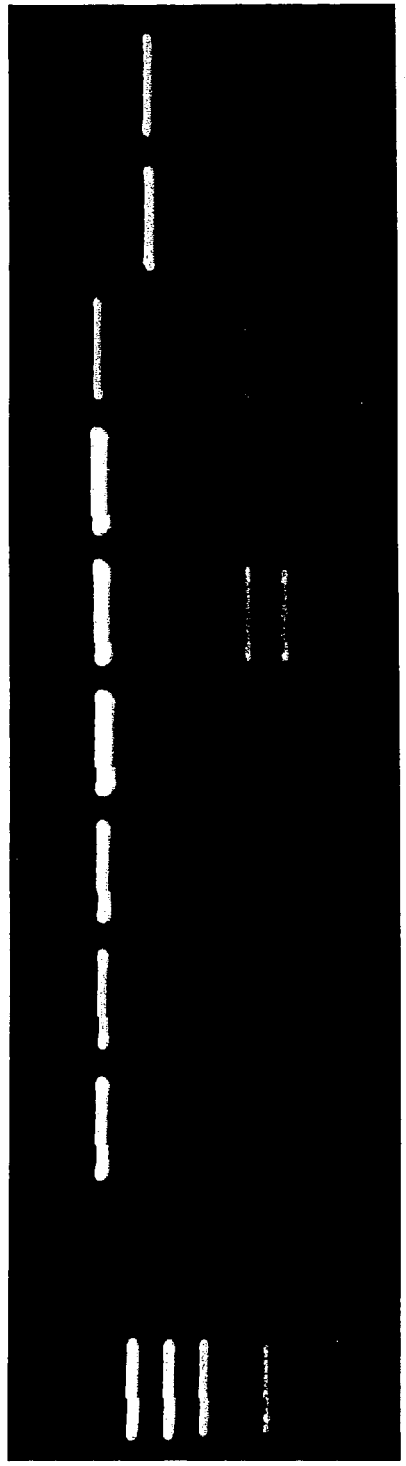
FIG. 1 shows migration photographs in electrophoresis after PCR to detect different varieties mixed in "Koshihikari" by the use of DNA groups for negative band discrimination. In this, M indicates a molecular marker; lane 1 is "Koshihikari"; lane 2 is "Hitomebore"; lane 3 is "Hinohikari"; lane 4 is "Akitakomachi"; lane 5 is "Kirara 397"; lane 6 is "Kinuhikari"; lane 7 is "Hoshinoyume"; lane 8 is "Haenuki"; lane 9 is "Mutsuhomare"; lane 10 is "Nipponbare"; lane 11 is "Sasanishiki"; lane 12 is "Tsugaruroman"; lane 13 is "Hanaechizen"; lane 14 is "Yumetsukushi"; lane 15 is "Hatsushimo"; lane 16 is "Asanohikari"; lane 17 is "Tsukinohikari"; lane 18 is "Aichinokaori"; lane 19 is "Matsuribare"; lane 20 is "Akiho".
Figure 1:
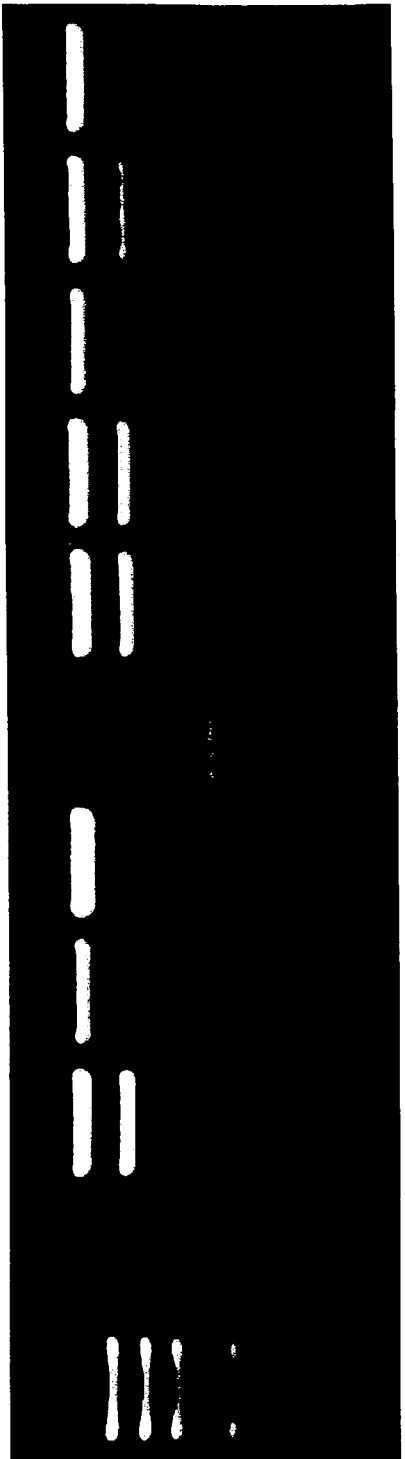

The invention is described in detail hereinunder.

The grains in the invention are meant to indicate seeds of true cereal (grains) such as rice, wheat, corn, barley and sorghum, including their processed products. The sample rice includes polished rice, unpolished rice, polished rice powder, unpolished rice powder, boiled rice and rice cake.

The object variety is meant to include mainstream varieties of grains. For rice, for example, it is high-quality rice of "Koshihikari", "Hitomebore", "Akitakomachi" and "Sasanishiki"; for barley, it includes "Ichibanboshi", "Sanshu" and "Daikei HK64"; and for corn, it includes "Honeybantam", "Petercorn" and "Waxycorn".

These grains are directly sampled as they are, or if desired, they may be ground into powder by the use of a suitable grinding machine such as ultracentrifugal grinder (by Retsch), cyclone mill (by UD), Millser (by Iwatani) or mortar, and the resulting powder is sampled.

For extracting a genome DNA from the grain sample, employable is any known DNA extraction process of, for example, phenol extraction, cetyltrimethylammonium bromide extraction (CTAB) or alkali SDS. In the invention, CTAB is preferred, as in the Examples given hereinunder.

For example, a CTAB solution (0.1 M tris-HCl, 2 mM disodium ethylenediaminetetraacetate (EDTA), 1.4M NaCl (pH8.0)) is added to a sample and stirred. This is put into an incubator, and the CTAB solution is again added thereto and left as it is for a predetermined period of time to extract the genome DNA from the sample.

In case where the sample is from boiled rice or rice cake, its genome DNA may be extracted according to an enzyme extraction process as in Japanese Patent No. 3,048,149. Concretely, the sample is homogenized, the (homogenized) sample is processed with heat-resistant amylase, and a genome gene is extracted from it.

If desired, the thus-extracted DNA may be purified, for example, through treatment with chloroform/isoamyl alcohol, or isopropanol precipitation, or protein removal with phenol/chloroform, or ethanol precipitation. For the purification, preferred is treatment with chloroform/isoamyl alcohol. Concretely, chloroform/isoamyl alcohol (24/1) is added to a DNA extract, stirred and centrifuged; a DNA precipitant is added to the resulting supernatant to precipitate the DNA; this is again centrifuged, and the resulting DNA precipitate is extracted with 1 M NaCl; and the DNA extract is washed with isopropyl alcohol and ethanol, then precipitated, and dissolved in a TE buffer. The process gives a purified DNA sample solution.

Subsequently, the genome DNA obtained as in the above is subjected to PCR in which it serves as a template in the presence of a random primer. This is for amplifying the base sequence of the genome DNA, which has an ability to discriminate variety and is the basis in planning the pair primers for the next PCR.

PCR in the invention is chain reaction with DNA polymerase for DNA replication. One cycle of PCR comprises three steps; a step of heating a template DNA at a high temperature falling between 90 and 96° C. or so in the presence of a heat-resistant DNA polymeraze and a primer (denaturation), a step of binding the primer to the DNA at about 30 to 75° C. (annealing), and a step of replicating the DNA at about 70 to 75° C. (chain-extension) In the invention, from 20 to 60 cycles of such PCR are repeated to amplify the template DNA to about 1,000,000 to 1,000,000,000 times.

In multiplex PCR, plural pair primers are combined and used. In this, plural pair primers (8- to 30-dimers) having a similar melting point are selected so that they do not form primer dimers and the discrimination bands formed do not interfere or overlap with each other. In that condition, the PCR frequency and the electrophoresis and staining frequency can be reduced.

The pair primer means a pair of primers having the function of amplifying the base sequence for variety discrimination in DNA. As so mentioned hereinabove, the pair primers are planned on the basis of the base sequence of DNA that gives a variety discrimination band. The DNA of each grain sample is sequenced through PCR according to RAPD method. Concretely, a genome DNA of an object grain is subjected to PCR in which it serves as a template in the presence of a random primer, and a part of the DNA that has given a variety discrimination band is sequenced. Of the base sequence, from 15 to 29 base residues on the forward side of the random primer and on the reverse side thereof are selected for a pair of primers. The pair primers are used in PCR for variety discrimination along with the template DNA of the object grain.

In that manner, the pair primers are specifically selected from the random primer that has plural sites to receive the template DNA. Therefore, in variety discrimination PCR of the template DNA, the thus-selected pair primers selectively bind to only the base sequence of the template DNA to give a variety discrimination band.

The random primer for use in the invention is described. In PCR of the genome DNA extracted from a grain sample in which the genome DNA serves as a template, the random primer used complimentarily binds to the denatured, single-stranded genome DNA to construct a double-stranded structure, and this serves as a start point of template DNA replication. In general, the random primer is a 8-to 50-mer nucleotide, and this is a synthetic primer constructed by binding adenine (A), thymine (T), guanine (G) and cytosine (C) at random. For example, it includes a 10-mer random primer (by Operon) and a DNA oligomer set (12-mer) (by Wako Pure Chemical Industries) available on the market.

Subsequently, the DNA thus amplified through such PCR is subjected to electrophoresis. This is for detecting the band of the base sequence for variety discrimination from the amplified products, and the thus-detected base sequence is to be the basis in planning the intended pair primers.

The electrophoresis is as follows: The amplified DNA through PCR products are allowed to migrate in agarose or polyacrylamide gel by a direct current applied thereto. In this, DNAs are separated from each other owing to the molecular weight difference between them, and stained with ethidium bromide to give bands. The bands indicate the difference of the amplified DNA from the others.

Based on the thus-detected band that indicates the base sequence for variety discrimination, a pair of primers are constructed as follows:

The DNA fragment having given the band of variety discrimination is cut out of the gel to extract and collect the DNA, and this is transformed into cells of *E. coli*. With the DNA therein, the transformant cells are grown. Next, the plasmid is extracted out of the cells according to an alkaline miniprep process. Serving as a template DNA, the plasmid is amplified through PCR, and then this is sequenced by the use of an automatic DNA sequencer.

Based on the thus-sequenced DNA, pair primers are planned. In the previous PCR with a random primer, the sequence that includes the site of the grain sample-derived DNA, or the template DNA, to which the random primer has bound should be the same as or complimentary (homologous) to that of the random primer. In other words, the DNA base sequence of high-quality variety discrimination that has been cut and extracted out of the electrophoresis gel (this is to be the basis of the pair primers in multiplex PCR) should have a sequence part that is the same as or homologous to the base sequence of the random primer at its both ends.

Accordingly, from both the forward side and the reverse side of the DNA base sequence of high-quality variety discrimination, pair primers having a suitable sequence and a suitable length that are useful for grain variety discrimination can be planned.

Regarding their size, it is desirable that the pair primers each have from 10 to 40 bases, more preferably from 13 to 29 bases. If their size oversteps the range, it is unfavorable since the primers could not well bind to the template DNA, and after bound thereto, the primers could not well dissociate from it, and, in addition, the DNA does not give a discrimination band in PCR and will be therefore useless for variety discrimination. On the other hand, if their size is smaller than the range, it is also unfavorable since the primers may non-specifically bind to some other unintended DNA fragments and may be mismatched with them, and, as a result, the band expression frequency not indicating the intended discrimination bands will increase. After all, such small-sized primers will be useless for rapid and simple variety discrimination in multiplex PCR using plural primers.

Through PCR experiments made to the effect as above, we, the present inventors have obtained various variety discrimination bands effective for discriminating grain varieties from each other. Table 1 below shows a correlation between rice variety discrimination bands and rice varieties that may be discriminated from each other on the basis of the bands.

TABLE 1-1

| Rice Variety Discrimination Band | A6 | A7 | B1 | B7 | B18 | B43 |
|---|---|---|---|---|---|---|
| band length (kbp) | 0.7 | 0.7 | 0.5 | 0.5 | 1.0 | 0.9 |
| Koshihikari | − | + | − | − | + | + |
| Hitomebore | − | + | − | − | + | + |
| Hinohikari | − | + | + | − | + | − |
| Akitakomachi | − | + | − | − | + | + |
| Kirara 397 | − | + | − | − | − | − |
| Kinuhikari | + | + | + | + | − | − |
| Hoshinoyume | − | + | − | − | − | − |
| Haenuki | + | + | − | − | − | − |
| Mutsuhomare | − | + | + | + | − | + |
| Nipponbare | − | − | + | − | − | + |
| Sasanishiki | − | + | − | + | − | + |
| Tsugaruroman | − | + | − | + | − | − |
| Hanaechizen | − | − | − | − | − | − |
| Yumetsukushi | − | + | + | − | + | + |
| Hatsushimo | + | + | + | − | − | + |
| Asanohikari | − | − | + | − | − | − |
| Tsukinohikari | − | − | + | − | − | + |
| Aichinokaori | + | + | − | − | − | + |
| Matsuribare | − | − | + | − | − | − |
| Akiho | − | + | − | − | − | + |

+: Discrimination band appeared in electrophoresis after PCR.
−: Discrimination band did not appear in electrophoresis after PCR.

TABLE 1-2

| Rice Variety Discrimination Band | E22 | E30 | F6 | G4 | G22 | G28 |
|---|---|---|---|---|---|---|
| band length (kbp) | 1.9 | 0.8 | 1.2 | 0.9 | 0.7 | 0.4 |
| Koshihikari | + | − | − | − | + | + |
| Hitomebore | + | + | − | − | + | + |
| Hinohikari | − | − | − | − | + | − |
| Akitakomachi | + | − | − | − | − | + |
| Kirara 397 | + | − | − | + | + | + |
| Kinuhikari | + | − | − | − | − | + |
| Hoshinoyume | − | − | − | − | + | + |
| Haenuki | + | − | − | − | − | + |
| Mutsuhomare | + | + | + | − | − | + |
| Nipponbare | − | − | + | − | − | − |
| Sasanishiki | − | − | − | − | + | − |
| Tsugaruroman | − | − | − | − | − | + |
| Hanaechizen | − | − | − | − | − | + |
| Yumetsukushi | − | − | − | − | − | + |
| Hatsushimo | + | − | − | − | − | − |
| Asanohikari | − | − | − | − | − | − |
| Tsukinohikari | − | − | + | − | − | − |
| Aichinokaori | + | − | + | − | − | − |
| Matsuribare | − | − | + | − | + | − |
| Akiho | − | − | − | + | + | − |

+: Discrimination band appeared in electrophoresis after PCR.
−: Discrimination band did not appear in electrophoresis after PCR.

TABLE 1-3

| Rice Variety Discrimination Band | J6 | M2CG | M11 | P3 | P5 | Q16 |
|---|---|---|---|---|---|---|
| band length (kbp) | 0.9 | 1.2 | 0.7 | 0.5 | 0.4 | 0.6 |
| Koshihikari | + | + | + | + | + | + |
| Hitomebore | + | + | + | − | + | + |
| Hinohikari | + | − | + | + | + | + |
| Akitakomachi | + | − | + | − | + | + |
| Kirara 397 | + | + | − | + | − | + |
| Kinuhikari | + | − | + | + | + | + |
| Hoshinoyume | + | + | − | + | − | − |
| Haenuki | + | + | + | − | + | + |
| Mutsuhomare | + | + | − | − | − | + |
| Nipponbare | + | + | − | + | − | − |
| Sasanishiki | − | − | + | − | − | + |
| Tsugaruroman | + | − | + | − | − | − |
| Hanaechizen | + | + | + | + | + | − |
| Yumetsukushi | + | − | − | + | + | − |
| Hatsushimo | + | + | + | + | + | − |
| Asanohikari | + | − | + | + | − | − |
| Tsukinohikari | + | + | − | + | − | − |
| Aichinokaori | + | + | + | + | − | − |
| Matsuribare | + | − | + | + | − | − |
| Akiho | + | + | − | + | − | − |

+: Discrimination band appeared in electrophoresis after PCR.
−: Discrimination band did not appear in electrophoresis after PCR.

TABLE 1-4

| Rice Variety Discrimination Band | S13 | T8 | T16 | WK9 | A52 |
|---|---|---|---|---|---|
| band length (kbp) | 1.8 | 0.9 | 1.6 | 1.6 | 1.0 |
| Koshihikari | − | − | − | − | − |
| Hitomebore | − | − | − | + | − |
| Hinohikari | − | − | − | + | − |
| Akitakomachi | − | − | − | + | + |
| Kirara 397 | + | + | + | + | + |
| Kinuhikari | − | + | + | + | − |
| Hoshinoyume | + | + | − | + | − |
| Haenuki | − | − | − | + | − |
| Mutsuhomare | − | + | + | − | − |
| Nipponbare | − | − | − | − | + |
| Sasanishiki | − | + | − | − | − |

TABLE 1-4-continued

| Rice Variety Discrimination Band | S13 | T8 | T16 | WK9 | A52 |
|---|---|---|---|---|---|
| Tsugaruroman | − | + | − | + | − |
| Hanaechizen | − | + | + | + | − |
| Yumetsukushi | − | + | + | + | − |
| Hatsushimo | − | + | + | − | − |
| Asanohikari | − | + | + | + | − |
| Tsukinohikari | − | − | + | + | − |
| Aichinokaori | − | − | + | + | − |
| Matsuribare | − | − | + | + | − |
| Akiho | − | − | + | + | − |

+: Discrimination band appeared in electrophoresis after PCR.
−: Discrimination band did not appear in electrophoresis after PCR.

Table 2 below shows a correlation between corn or barley variety discrimination bands and corn or barley varieties that may be discriminated from each other on the basis of the bands.

TABLE 2-1

| Corn or Barley Variety Discrimination Band | WK9 | A6 | M2CG | G4 | S13 |
|---|---|---|---|---|---|
| band length (kbp) | 1.6 | 0.7 | 1.2 | 0.9 | 1.8 |
| Honeybantam | − | + | + | − | − |
| Petercorn | + | − | − | − | − |
| Waxycorn | − | + | + | + | + |
| Ichibanboshi | − | − | − | − | − |
| Sanshu | + | − | − | − | − |
| Daikei HK64 | − | − | + | + | − |

+: Discrimination band appeared in electrophoresis after PCR.
−: Discrimination band did not appear in electrophoresis after PCR.

TABLE 2-2

| Corn or Barley Variety Discrimination Band | F6 | E30 | A7 | B7 | J6 |
|---|---|---|---|---|---|
| band length (kbp) | 1.2 | 0.8 | 0.7 | 0.5 | 0.9 |
| Honeybantam | − | − | − | + | − |
| Petercorn | − | − | − | − | + |
| Waxycorn | + | + | + | − | + |
| Ichibanboshi | − | − | − | − | + |
| Sanshu | − | − | − | − | − |
| Daikei HK64 | + | − | − | − | + |

+: Discrimination band appeared in electrophoresis after PCR.
−: Discrimination band did not appear in electrophoresis after PCR.

From these bands, various pair primers were obtained.

(1) Discrimination Band A7 (0.7 kbp):

This band is given by the amplified DNAs from rice varieties "Koshihikari" and "Akitakomachi", but not by those from "Nipponbare" and "Asanohikari". From the band A7, a pair of primers A7F30 (SEQ ID NO. 5) and A7R30 (SEQ ID NO. 6) were planned.

Next, a predetermined number of bases were deleted from the 3'-side of the primers to obtain pair primers for use in the invention, A7F19 (SEQ ID No. 7) and A7R16 (SEQ ID No. 8).

(2) Discrimination Band B43 (0.9 kbp):

This band is given by the amplified DNAs from rice varieties "Koshihikari", "Hitomebore" and "Sasanishiki", but not by those from "Kirara 397" and "Asanohikari". From the band B43, a pair of primers B43F30 (SEQ ID No. 25) and B43R30 (SEQ ID No. 26) were planned.

Next, a predetermined number of bases were deleted from the 3'-side of the primers to obtain pair primers for use in the invention, B43F17' (SEQ ID No. 27) and B43R18 (SEQ ID No. 28).

(3) Discrimination Band E30 (0.85 kbp):

This band is given by the amplified DNAs from rice varieties "Hitomebore" and "Mutsuhomare", but not by those from "Koshihikari" and "Akitakomachi". From the band E30, a pair of primers E30F30 (SEQ ID No. 37) and E30R30 (SEQ ID No. 38) were planned.

Next, some bases were deleted from the primers to obtain pair primers for use in the invention, E30F28 (SEQ ID No. 39) and E30R24 (SEQ ID No. 40).

(4) Discrimination Band J6 (0.9 kbp):

This band is given by the amplified DNAs from rice varieties "Koshihikari" and "Kirara 397", but not by those from "Sasanishiki". From the band J6, a pair of primers J6F30 (SEQ ID No. 57) and J6R30 (SEQ ID No. 58) were planned.

Next, some bases were deleted from the primers to obtain pair primers for use in the invention, J6F18 (SEQ ID No. 59) and J6R20 (SEQ ID No. 60).

(5) Discrimination Band M2CG (1.2 kbp):

This band indicates addition of two bases to a 10-mer random primer, and this is given by the amplified DNAs from rice varieties "Hitomebore" and"Nipponbare" but not by those from"Koshihikari" and "Kinuhikari". From the band M2CG, a pair of primers M2CGF30 (SEQ ID No. 61) and M2CGR30 (SEQ ID No. 62) were planned.

Next, some bases were deleted from the primers to obtain pair primers for use in the invention, M2CGF16 (SEQ ID No. 63) and M2CCG15 (SEQ ID No. 64).

(6) Discrimination Band S13 (1.8 kbp):

This band is given by the amplified DNAs from rice varieties "Kirara 397" and "Hoshinoyume", but not by those from "Nipponbare" and "Asanohikari". From the band S13, a pair of primers S13F30 (SEQ ID No. 81) and S13R30 (SEQ ID No. 82) were planned.

Next, some bases were deleted from the primers to obtain pair primers for use in the invention, S13F25 (SEQ ID No. 83) and S13R24 (SEQ ID No. 84).

(7) Discrimination Band WK9 (1.6 kbp):

This Band is given by the amplified DNAs from rice varieties "Hitomebore" and "Akitakomachi", but not by those from "Koshihikari" and "Sasanishiki". From the band WK9, a pair of primers WK9F30 (SEQ ID No. 93) and WK9R30 (SEQ ID No. 94) were planned.

Next, some bases were deleted from the primers to obtain pair primers for use in the invention, WK9F (SEQ ID No. 95) and WK9R20(SEQ ID No. 96).

The primers mentioned above were planned on the basis of rice bands, but most of them are usable also for variety discrimination of corn or barley that are belonging to the same Gramineae.

For obtaining the pair primers for use in the invention, some bases are deleted from the specifically planned primers as above. Briefly, a template DNA extracted from a grain sample is amplified, and a pair of primers are planned on the basis of the amplified DNA. 1 to 17 bases are deleted from the 3'-side of the thus-planned primers to give pair primers of from 13 to 29 bases each. The pair primers are used in the invention.

Deleting the bases may be effected in any ordinary manner using suitable restriction endonuclease.

Concretely, from pairs of primers, A6F30 (SEQ ID No. 1) and A6R30 (SEQ ID No. 2); A7F30 (SEQ ID No. 5) and A7R30 (SEQ ID No. 6); A52F30 (SEQ ID No. 9) and A52R30 (SEQ ID No. 10); B1F30 (SEQ ID No. 13) and B1R30 (SEQ ID No. 14); B7F30 (SEQ ID No. 17) and B7R30 (SEQ ID No. 18); B18F30 (SEQ ID No. 21) and B18R30 (SEQ ID No. 22); B43F30 (SEQ ID No. 25) and F43R30 (SEQ ID No. 26); D4F30 (SEQ ID No. 29) and D4R30 (SEQ ID No. 30); E22F30 (SEQ ID No. 33) and E22R30 (SEQ ID No. 34); E30F30 (SEQ ID No. 37) and E30R30 (SEQ ID No. 38); F6F30 (SEQ ID No. 41) and F6R30 (SEQ ID No. 42); G4F30 (SEQ ID No. 45) and G4R30 (SEQ ID No. 46); G22F30 (SEQ ID No. 49) and G22R30 (SEQ ID No. 50); G28F30 (SEQ ID No. 53) and G28R30 (SEQ ID No. 54); J6F30 (SEQ ID No. 57) and J6R30 (SEQ ID No. 58); M2CGF30 (SEQ ID No. 61) and M2CGR30 (SEQ ID No. 62); M11F30 (SEQ ID No. 65) and M11R30 (SEQ ID No. 66); P3F30 (SEQ ID No. 69) and P3R30 (SEQ ID No. 70); P5F30 (SEQ ID No. 73) and P5R30 (SEQ ID No. 74); Q16F30 (SEQ ID No. 77) and Q16R30 (SEQ ID No. 78); S13F30 (SEQ ID No. 81) and S13R30 (SEQ ID No. 82); T8F30 (SEQ ID No. 85) and T8R30 (SEQ ID No. 86); T16F30 (SEQ ID No. 89) and T16R30 (SEQ ID No. 90); WK9F30 (SEQ ID No. 93) and WK9R30 (SEQ ID No. 94), 1 to 17 bases are deleted on their 3'-side according to the method mentioned above to give pair primers each composed of 13 to 29 bases. From the group of these pair primers, at least two pair primers are selected and used in the invention.

Accordingly, the pair primers for use in the invention are at least two or more oligonucleotides selected from a group of A6F21 (SEQ ID No. 3) and A6R22 (SEQ ID No. 4); A7F19 (SEQ ID No. 7) and A7R16 (SEQ ID No. 8); A52F29 (SEQ ID No. 11) and A52R21 (SEQ ID No. 12); B1F25 (SEQ ID No. 15) and B1R20 (SEQ ID No. 16); B7F22 (SEQ ID No. 19) and B7R17 (SEQ ID No. 20); B18F15 (SEQ ID No. 23) and B18R21 (SEQ ID No. 24); B43F17 (SEQ ID No. 27) and B43R18 (SEQ ID No. 28); D4F23 (SEQ ID No. 31) and D4R21 (SEQ ID No. 32); E22F20 (SEQ ID No. 35) and E22R21 (SEQ ID No. 36); E30F28 (SEQ ID No. 39) and E30R24 (SEQ ID No. 40); F6F25 (SEQ ID No. 43) and F6R22 (SEQ ID No. 44); G4F18 (SEQ ID No. 47) and G4R24 (SEQ ID No. 48); G22F27 (SEQ ID No. 51) and G22R23 (SEQ ID No. 52); G28F17 (SEQ ID No. 55) and G28R28 (SEQ ID No. 56); J6F18 (SEQ ID No. 59) and J6R20 (SEQ ID No. 60); M2CGF16 (SEQ ID No. 63) and M2CGR15 (SEQ ID No. 64); M11F20 (SEQ ID No. 67) and M11R20 (SEQ ID No. 68); P3F20 (SEQ ID No. 71) and P3R15 (SEQ ID No. 72); P5F20 (SEQ ID No. 75) and P5R25 (SEQ ID No. 76); Q16F25 (SEQ ID No. 79) and Q16R20 (SEQ ID No. 80); S13F25 (SEQ ID No. 83) and S13R24 (SEQ ID No. 84); T8F22 (SEQ ID No. 87) and T8R25 (SEQ ID No. 88); T16F24 (SEQ ID No. 91) and T16R26 (SEQ ID No. 92); WK9F20 (SEQ ID No. 95) and WK9R20 (SEQ ID No. 96).

The pair primers for use in the invention are not limited to those mentioned above. Any other additional pair primers suitable to the invention may be planned in consideration of their capability for variety discrimination and their melting temperature (Tm), and may be used in the invention.

Tm corresponds to the temperature at which the two strands of DNA are separated from each other. For the annealing temperature in PCR, in general, Tm or thereabout of the primers used therein is suitable. In the method of the invention, pair primers having a similar Tm are specifically selected and used, and the annealing temperature in PCR of DNA in the method is suitably so determined that it is near to Tm of the pair primers used. Therefore, in the method of the invention, the intended discrimination band to be given in a process where the pair primers are separately used can be obtained in one or a few PCR cycles.

Concretely, it is desirable that the difference between the average Tm of the pair primers to be used in the invention and Tm of each pair primer is not larger than 15° C. (±15° C.), and the annealing temperature in PCR also falls within the range.

If the annealing temperature in PCR is lower by 15° C. or more than the mean Tm of the pair primers used, it is unfavorable since the varieties that should not give discrimination bands may give them through PCR. On the other hand, if the annealing temperature in PCR is higher by 15° C. or more than the mean Tm of the pair primers used, it is also unfavorable since the discrimination band that should be given may disappear through PCR.

In the invention, the template DNA previously extracted from a grain sample is subjected to multiplex PCR in the presence of pair primers.

Suitably selected, the pair primers selectively bind, in PCR, to only the base sequence site of the DNA that gives a variety discrimination band, and therefore make it possible to discriminate the object grain variety of the invention from any others.

In the invention, one or more different combinations of such pair primers can be used.

Using different combinations of pair primers in the invention means that the selected different combinations of pair primers are used in one and the same reaction in PCR for variety discrimination. In the conventional process of RAPD, many common bands appear apart from the intended discrimination band, and therefore it is difficult to use plural primers at the same time. In the invention, specifically selected combinations of pair primers (as a primer set) are used and a discrimination band corresponding to each primer used appears through electrophoresis. Therefore, the invention has made it possible to use different combinations of pair primers for grain variety discrimination.

All the pair primers prepared could not be combined unconditionally. It is necessary to suitably combine the pair primers in a suitably selected blend ratio, taking the matters into consideration that the primers combined should not form primer dimers and the discrimination bands to appear should not overlap with each other. Suitably combining various pair primers and using the thus-combined pair primers removes the necessity of PCR for every primer, and makes it possible to accurately and rapidly discriminate many grain varieties from each other in only one PCR. To that effect, the invention significantly saves the labor, the time and the cost for grain variety discrimination.

In the invention, the positive band to be specifically given by only the object variety is meant to indicate the band that specifically appears in the band pattern given by the object variety, and the band pattern having the positive band is specific to the object variety.

For example, in case where a pair primer set of four pair primers of WK9, M11, B43 and G22 is used for an object variety "Koshihikari", a grain sample of "Koshihikari" alone does not give a discrimination band of WK9, but gives three discrimination bands of M1, B43 and G22. This discrimination band pattern is not given by any other grain varieties, and this is specific to the variety "Koshihikari" only.

The pair primer set for positive band discrimination that gives a specific positive band for the object variety alone, and the pair primer set for negative band discrimination that gives no band for the object variety alone are the primer sets that give a specific band pattern specific to the object variety only as in the above.

The above case is investigated for the probability that the grain sample tested may be presumed the object variety "Koshihikari" alone. When the discrimination band expression probability in the case is presumed 0.5 of expression/non-expression, the probability that any other variety than "Koshihikari" will accidentally give the same band pattern as that of the object variety "Koshihikari" in point of all the four discrimination bands is (0.5) 4, or that is, 0.0625.

From this, it can be presumed that, when the four band patterns of an unknown grain sample tested are all the same as those of the object variety, the grain sample will be just the object variety at a probability of 90% or more.

The negative bands not given by the object variety are meant to indicate the bands that appear in the band patterns given by any other varieties than the object variety, but specifically not in the band patterns given by the object variety.

For example, in case where a pair primer set of four pair primers, WK9F20 (SEQ ID No. 95) and WK9R20 (SEQ ID No. 96); F6F25 (SEQ ID No. 43) and F6R22 (SEQ ID No. 44); B7F22 (SEQ ID No. 19) and B7R17 (SEQ ID No. 20); A6F21 (SEQ ID No. 3) and A6R22 (SEQ ID No. 4), is used for an object variety "Koshihikari", a grain sample of "Koshihikari" alone gives no band of amplified DNA after PCR.

On the other hand, when the grain samples tested in that case are any others than "Koshihikari", they give some discrimination bands of the pair primers used. Concretely, when the grain sample tested is "Kirara 397", it gives a discrimination band of WK9; when "Kinuhikari", it gives discrimination bands of WK9 and B7; and when "Mutsuhomare", it gives a discrimination band of B7.

In the above case, when the grain sample tested gave no discrimination band in primary PCR using pair primers for negative band discrimination, but in secondary PCR using any other pair primers as in Tables 1 and 2 above, if the discrimination band patterns of the grain sample tested are the same as those of the object variety "Koshihikari", the probability that the grain sample tested is "Koshihikari" is extremely high.

For example, when four pair primers are used for a pair primer group for negative band discrimination that gives no discrimination band for the object variety "Koshihikari" and four pair primers are also used for a pair primer group for positive band discrimination that gives discrimination bands specific to only the object variety or for that for negative band discrimination that gives no discrimination band specifically to only the object variety, and when a grain sample tested with the former group gives no discrimination band but the discrimination patterns thereof tested with the latter are the same as those of the object variety "Koshihikari", then the probability P that the grain sample tested is not "Koshihikari" is $(\frac{1}{2})^4 \times (\frac{1}{2})^4 = 0.0039$, or that is smaller than 0.01.

Accordingly, when a grain sample tested through PCR with such a pair primer group for negative band discrimination that gives no discrimination band for the object variety "Koshihikari" gave no discrimination band, and when the same grain sample further tested through PCR with a pair primer group for positive band discrimination that gives discrimination bands specific to only the object variety or for that for negative band discrimination that gives no discrimination band specifically to only the object variety gave the same discrimination band patterns as those of the object variety, then it should be presumed that the grain sample tested is "Koshihikari" at a probability higher than 99.9%.

Next described is a method of identifying the mixed variety in a grain sample that contains it mixed with the object variety of the sample.

For example, a sample of mixed rice of two varieties, "Mutsuhomare" and "Koshihikari" is tested with a pair primer set of four pair primers, WK9, M11, G22 and B43, which are for positive band discrimination specific to the object variety. M11 and G22 give discrimination bands with "Koshihikari" but give no discrimination band with "Mutsuhomare" when the two varieties are tested individually. Based on this, the two varieties in the mixed rice sample can be differentiated from each other.

However, when a small quantity of "Mutsuhomare" is mixed with "Koshihikari" and when the mixed rice is tested with the pair primer set, the negativity of "Mutsuhomare" that it gives no discrimination band with the primers M11 and G22 is hidden by the extensive positive bands given by "Koshihikari", and it is impossible to detect the presence of "Mutsuhomare" in the mixed rice.

Therefore, for identifying a different variety in such mixed rice, the pair primer groups described in Japanese Patent Laid-Open No.2001-95589 are unsatisfactory, since they are for separately testing different varieties of rice to thereby differentiate one variety from the others. The intended identification of a different variety in mixed rice additionally requires a pair primer group for negative band discrimination that gives no discrimination band for the object variety but gives some discrimination bands for the different variety.

The present invention has made it possible to detect the presence or absence of any different varieties mixed in grains of rice, wheat, corn or barley and to identify the mixed varieties through multiplex PCR of DNAs extracted from the grains. Specifically, the invention comprises primary PCR to rapidly and simply detect the presence or absence of even a small amount of any different varieties mixed in grains, optionally followed by secondary PCR to identify the mixed varieties.

In particular, since the PCR in the invention uses pair primers highly effective for variety discrimination, it enables accurate variety identification even when the discrimination bands other than those of the object variety have disappeared, for example, as in the case of mixed rice of "Koshihikari"-related varieties.

Moreover, since the PCR in the invention is multiplex PCR that uses different pair primers combined, the PCR frequency and also the electrophoresis frequency and staining frequency can be reduced. Therefore, the time for variety discrimination in the invention can be shortened and the cost for it can be reduced.

EXAMPLES

The invention is described in more detail with reference to the following Examples, which, however, are not intended to restrict the scope of the invention.

Example 1

(Detection of Different Varieties Mixed in "Koshihikari" by the use of DNA Groups for Negative Band Discrimination):

Best twenty varieties of rice harvested in 1999 in Japan, "Koshihikari", "Hitomebore", "Hinohikari", "Akitakomachi", "Kirara 397", "Kinuhikari", "Hoshinoyume", "Haenuki", "Mutsuhomare", "Nipponbare", "Sasanishiki", "Tsugaruroman", "Hanaechizen", "Yumetsukushi", "Hatsushimo", "Asanohikari", "Tsukinohikari", "Aichinokaori", "Matsuribare" and "Akiho" were tested, all unpolished. Using a laboratory rice mill, (Yamamoto Seisakusho's Ricepal VP31T), these were milled into polished rice to a yield of 90%.

Using an ultracentrifugal grinder (by Retsch), the polished rice samples were separately ground. A genome DNA was extracted from 6 g of each powder sample through CTAB treatment. Concretely, 6 ml of a 2% CTAB solution (0.1 M tris-HCl, 2 mM disodium ethylenediaminetetraacetate (EDTA), 1.4M NaCl, pH 8.0) at 70° C. was added to the sample and stirred, and put into an incubator at 55° C., and 6 ml of the same CTAB (1%) solution was added thereto. In that condition, the genome DNA was extracted from the sample for 30 minutes.

Next, chloroform/isoamyl alcohol (24/1) was added to the DNA extract, stirred and centrifuged. A DNA precipitant (1% CTAB, 20 mM tris-HCl, 10 mM EDTA, pH 8.0) was added to the resulting supernatant, and left at 4° C. overnight to precipitate the DNA. Next, this was centrifuged, and the resulting DNA precipitate was extracted with 1 M NaCl. The DNA extract was washed with isopropyl alcohol and ethanol, then precipitated, and dissolved in 200 μl of a TE buffer (10 mM tris-HCl, 1 mM EDTA, pH 8.0) to prepare a DNA sample solution.

A PCR composition was prepared by mixing 11.74 μl of sterilized water, 0.2 μl of polymerase (Taq polymerase (5 U/μl) by Takara Bio Inc.), 2.5 μl of PCR buffer (12 mM tris-HCl, 60 mM KCl, pH 8.3), 2.0 μl of $MgCl_2$, 200 ng/1 μl of the template DNA, and 1 μl of dNTPs (100 μM). The pair primers for PCR are WK9F20 and WK9R20 (SEQ ID Nos. 95 and 96) of 0.6 μl each; F6F25 and F6R22 (SEQ ID Nos. 43 and 44) of 0.5 μl each; B7F22 and B7R17 (SEQ ID Nos. 19 and 20) of 0.5 μl each; and A6F21 and A6R22 (SEQ ID Nos. 3 and 4) of 0.4 μl each. These pair primers were mixed with the PCR composition to be 22.44 μl in total.

The reactor is PCR Thermal Cycler MP (by Takara Bio Inc.) In the reactor, the template DNA was subjected to 35-cycle PCR. One PCR cycle comprises denaturation at 94° C. for 1 minute, annealing at 62° C. for 1 minute and chain-extension at 72° C. for 2 minutes. The amplified DNA was then subjected to electrophores is in Mupid II (by Cosmobio), in which it was allowed to migrate in 2% agarose gel for 40 minutes, and stained with ethidium bromide to give a band pattern through exposure to UV light. The test results are shown in Table 3 and FIG. 1.

The results confirm that the 19 varieties except "Koshihikari" all gave some positive bands. This means that the mixed rice in "Koshihikari" can be detected according to the process of this Example.

On the other hand, in Example 10 of Japanese Patent Laid-Open No. 2001-95589 in which three primers of M2CG, WK9 and B7 were combined and used, both "Koshihikari" and "Hatsushimo" do not give a discrimination band. Therefore, when "Hatsushimo" is mixed with "Koshihikari", the two could not be discriminated from each other according to the process of that Example 10. From this, it is obvious that the method of the invention is superior to the method described in Japanese Patent Laid-Open No. 2001-95589.

TABLE 3

Data of PCR with Four Primers Combined

| Variety | WK9 | F6 | B7 | A6 |
|---|---|---|---|---|
| Koshihikari | − | − | − | − |
| Hitomebore | + | − | − | − |
| Hinohikari | + | − | − | − |
| Akitakomachi | + | − | − | − |
| 0Kirara 397 | + | − | − | − |
| Kinuhikari | + | − | + | + |
| Hoshinoyume | + | − | − | − |
| Haenuki | + | − | − | + |
| Mutsuhomare | − | + | + | − |
| Nipponbare | − | + | − | − |
| Sasanishiki | − | − | + | − |
| Tsugaruroman | + | + | + | − |
| Hanaechizen | + | − | − | − |
| Yumetsukushi | + | − | − | − |
| Hatsushimo | − | − | − | + |
| Asanohikari | + | + | − | − |
| Tsukinohikari | + | + | − | − |
| Aichinokaori | + | − | − | − |
| Matsuribare | + | + | − | − |
| Akiho | + | − | − | − |

+: Discrimination band appeared.
−: Discrimination band did not appear.

Example 2

(Discrimination of Different Varieties in Mixed Rice by the use of DNA Groups for Negative/Positive Band Discrimination):

Best twenty varieties of rice harvested in 1999 in Japan, "Koshihikari", "Hitomebore", "Hinohikari", "Akitakomachi", "Kirara 397", "Kinuhikari", "Hoshinoyume", "Haenuki", "Mutsuhomare", "Nipponbare", "Sasanishiki", "Tsugaruroman", "Hanaechizen", "Yumetsukushi", "Hatsushimo", "Asanohikari", "Tsukinohikari", "Aichinokaori", "Matsuribare" and "Akiho" were tested, all unpolished. Using a laboratory rice mill, (Yamamoto Seisakusho's Ricepal VP31T), these were milled into polished rice to a yield of 90%. One grain of each polished rice sample was ground in a mortar to prepare powder rice samples. A genome DNA was extracted from each powder sample, using a DNA extraction kit, ISOPLANT II.

A PCR composition was prepared by mixing 10.4 μl of sterilized water, 0.2 μl of polymerase (Taq polymerase (5 U/μl) by Takara Bio Inc.), 2.5 μl of PCR buffer (12 mM tris-HCl, 60 mM KCl, pH 8.3), 2.0 μl of MgCl$_2$, 1 μl of the template DNA (200 ng/μl), and 1 μl of dNTPs (100 μM). The pair primers for PCR are WK9F20 and WK9R20 (SEQ ID Nos. 95 and 96) of 0.6 μl each; M11F20 and M11R20 (SEQ ID Nos. 67 and 68) of 0.3 μl each; G22F27 and G22R23 (SEQ ID Nos. 51 and 52) of 0.3 μl each; B43F17 and B43R18 (SEQ ID Nos. 27 and 28) of 0.1 μl each; and P3F20 and P3R15 (SEQ ID Nos. 71 and 72) of 0.3 μl each. These pair primers were mixed with the PCR composition to be 20.3 μl in total.

The reactor is PCR Thermal Cycler MP (by Takara Bio Inc.). In the reactor, the template DNA was subjected to 35-cycle PCR. One PCR cycle comprises denaturation at 94° C. for 1 minute, annealing at 62° C. for 1 minute and chain-extension at 72° C. for 2 minutes.

Figure 2:
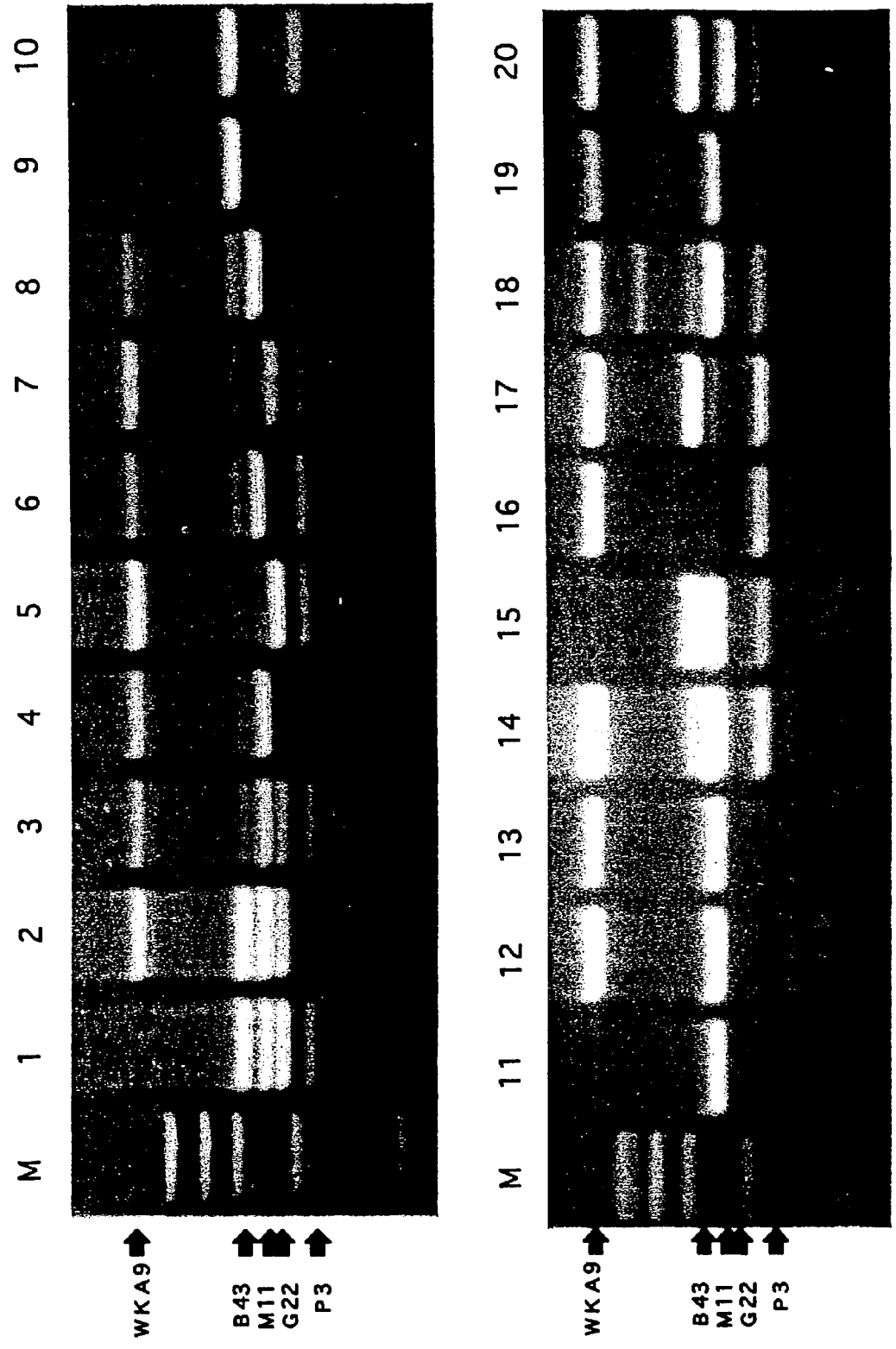
FIG. 2 shows migration photographs in electrophoresis after PCR to discriminate different varieties in mixed rice by the use of DNA groups for negative/positive band discrimination. In this, M indicates a molecular marker; lane 1 is "Koshihikari"; lane 2 is "Hitomebore"; lane 3 is "Hinohikari"; lane 4 is "Akitakomachi"; lane 5 is "Kirara 397"; lane 6 is "Kinuhikari"; lane 7 is "Hoshinoyume"; lane 8 is "Haenuki"; lane 9 is "Mutsuhomare"; lane 10 is "Nipponbare"; lane 11 is "Sasanishiki"; lane 12 is "Tsugaruroman"; lane 13 is "Hanaechizen"; lane 14 is "Yumetsukushi"; lane 15 is "Hatsushimo"; lane 16 is "Asanohikari"; lane 17 is "Tsukinohikari"; lane 18 is "Aichinokaori"; lane 19 is "Matsuribare"; lane 20 is "Akiho".

The amplified DNA was then subjected to electrophoresis in Mupid II (by Cosmobio), in which it was allowed to migrate in 2% agarose gel for 40 minutes, and stained with ethidium bromide to give a band pattern through exposure to UV light. The test results are shown in Table 4 and FIG. 2.

TABLE 4

Data of PCR with Five Primers Combined

| Variety | WK9 | M11 | G22 | B43 | P3 |
|---|---|---|---|---|---|
| Koshihikari | − | + | + | + | + |
| Hitomebore | + | + | + | + | − |
| Hinohikari | + | + | + | + | + |
| Akitakomachi | + | + | − | + | − |
| Kirara 397 | + | − | + | − | + |
| Kinuhikari | + | + | − | + | + |
| Hoshinoyume | + | − | + | + | + |
| Haenuki | + | + | − | + | − |
| Mutsuhomare | − | − | − | + | − |
| Nipponbare | − | − | − | + | + |
| Sasanishiki | − | + | − | − | − |
| Tsugaruroman | + | + | − | − | − |
| Hanaechizen | + | + | − | − | − |
| Yumetsukushi | + | + | − | + | + |
| Hatsushimo | − | + | − | + | + |
| Asanohikari | + | − | − | − | + |
| Tsukinohikari | + | − | − | + | + |
| Aichinokaori | + | + | − | + | + |
| Matsuribare | + | + | − | − | − |
| Akiho | + | − | + | + | + |

+: Discrimination band appeared.
−: Discrimination band did not appear.

The results confirm that, when the four primers WK9, F6, A6 and B7 used in Example 1 are combined with the pair primer set of four primers, M11, G22, B43 and P3 used in this Example, all the best twenty varieties of rice harvested in Japan can be discriminated from each other, except "Hoshinoyume" and "Akiho".

Accordingly, combining Examples 1 and 2 makes it possible to detect the presence or absence of mixed rice in "Koshihikari" and to identify almost all the different varieties of the mixed rice therein.

Example 3

(Detection of Mixed Rice by the use of Three DNA for Negative Band Discrimination):

Best twenty varieties of rice harvested in 1999 in Japan, "Koshihikari", "Hitomebore", "Hinohikari", "Akitakomachi", "Kirara 397", "Kinuhikari", "Hoshinoyume", "Haenuki", "Mutsuhomare", "Nipponbare", "Sasanishiki", "Tsugaruroman", "Hanaechizen", "Yumetsukushi", "Hatsushimo", "Asanohikari", "Tsukinohikari", "Aichinokaori", "Matsuribare" and "Akiho" were tested, all unpolished. In the same manner as in Example 1, a template DNA was prepared from each polished rice sample.

Figure 3:
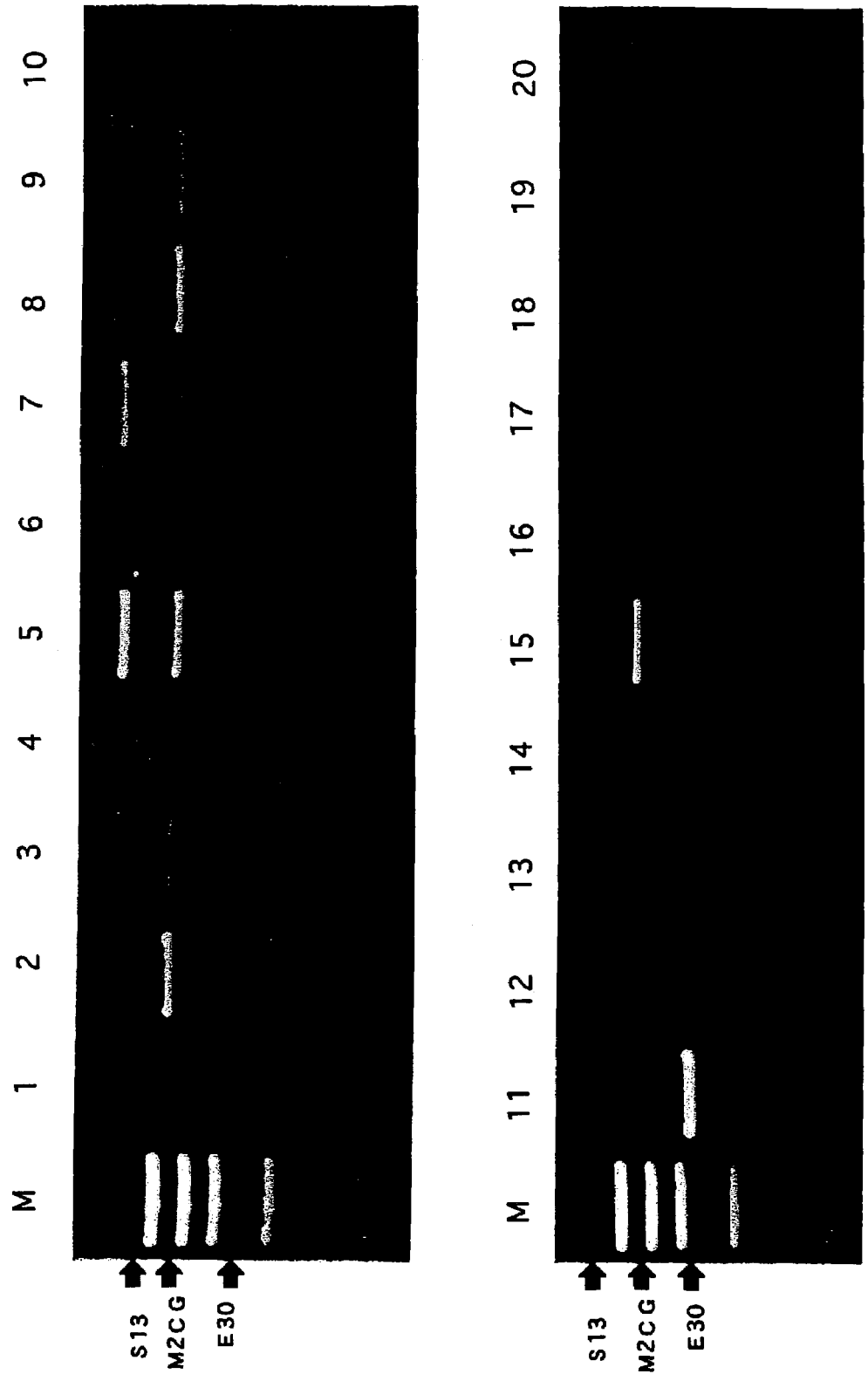
FIG. 3 shows migration photographs in electrophoresis after PCR to detect mixed rice in "Koshihikari" by the use of DNA groups for negative band discrimination. In this, M indicates a molecular marker; lane 1 is "Koshihikari"; lane 2 is "Hitomebore"; lane 3 is "Hinohikari"; lane 4 is "Akitakomachi"; lane 5 is "Kirara 397"; lane 6 is "Kinuhikari"; lane 7 is "Hoshinoyume"; lane 8 is "Haenuki"; lane 9 is "Mutsuhomare"; lane 10 is "Nipponbare"; lane 11 is "Sasanishiki"; lane 12 is "Tsugaruroman"; lane 13 is "Hanaechizen"; lane 14 is "Yumetsukushi"; lane 15 is "Hatsushimo"; lane 16 is "Asanohikari"; lane 17 is "Tsukinohikari"; lane 18 is "Aichinokaori"; lane 19 is "Matsuribare"; lane 20 is "Akiho".

In this Example, mixed rice of "Koshihikari" with a small amount of a different variety was estimated and tried. For this, 80% of DNA of "Koshihikari" was mixed with 20% of DNA of any other different variety to prepare a template DNA. The Template DNA was subjected to PCR with a primer mixture of S13F25 and S13R24 (SEQ ID Nos. 83 and 84) of 0.08 μl each; E30F28 and E30R24 (SEQ ID Nos. 39 and 40) of 0.05 μl each; and M2CGF16 and M2CGR22 (SEQ ID Nos. 63 and 64) of 1.0 μl each. The test results are shown in Table 5 and FIG. 3.

TABLE 5

Data of PCR with Three Primers Combined

| Variety | Primer | | |
|---|---|---|---|
| | S13 | E30 | M2CG |
| Koshihikari | − | − | − |
| Hitomebore | − | − | + |
| Hinohikari | − | − | + |
| Akitakomachi | − | − | − |
| Kirara 397 | + | − | + |
| Kinuhikari | − | − | − |
| Hoshinoyume | + | − | + |
| Haenuki | − | − | + |
| Mutsuhomare | − | − | + |
| Nipponbare | − | − | + |
| Sasanishiki | − | + | − |
| Tsugaruroman | − | − | − |
| Hanaechizen | − | − | + |
| Yumetsukushi | − | − | − |
| Hatsushimo | − | − | + |
| Asanohikari | − | − | − |
| Tsukinohikari | − | − | − |
| Aichinokaori | − | + | + |
| Matsuribare | − | − | − |
| Akiho | − | − | + |

+: Discrimination band appeared.
−: Discrimination band did not appear.

As in Table 5, the best twenty varieties except "Akitakomachi", "Kinuhikari", "Tsugaruroman", "Yumetsukushi", "Asanohikari", "Matsuribare" and "Tsukinohikari" all gave positive bands to the primer sets tested herein for mixed rice detection in "Koshihikari". The results confirm that the primer sets are useful for detection of mixed rice in "Koshihikari".

When the three primers used in this Example are combined with the primer set of nine primers used in Examples 1 and 2, then "Hoshinoyume" and "Akiho" that could not be discriminated in Example 2 can be discriminated, and the proposed combination is effective for identifying the individual varieties of mixed rice.

On the other hand, PCR in Example 1 of Japanese Patent Laid-Open No. 2001-95589 uses M2CG and S13 only. In this case, "Koshihikari" could be discriminated from "Nipponbare" and "Kirara 397", but could not from the other eight varieties "Akitakomachi", "Kinuhikari", "Sasanishiki", "Tsugaruroman", "Yumetsukushi", "Asanohikari", "Tsukinohikari" and "Matsuribare" since these eight varieties gave no discrimination band like "Koshihikari", as in Table 3 in the laid-open specification. From this, it is obvious that the process of Example 1 of Japanese Patent Laid-Open No. 2001-95589 is inferior to the process of this Example of the present invention.

Example 4

(Detection of Mixed Rice in Boiled Rice Samples and Identification of the Varieties of the Mixed Rice by the use of Negative Band Groups and Negative/Positive Band Groups Combined):

Twenty varieties of rice harvested in Japan including best ten varieties of rice harvested in Japan, "Koshihikari", "Hitomebore", "Hinohikari", "Akitakomachi", "Kirara 397", "Kinuhikari", "Hoshinoyume", "Haenuki", "Mutsuhomare" and "Nipponbare" were tested, all unpolished. Using a laboratory rice mill, (Yamamoto Seisakusho's Ricepal VP31T), these were milled into polished rice to a yield of 90%.

One grain of each polished rice sample was put into a plastic tube (by Assist, 1.5 ml volume), and 35 μl of deionized water was added thereto. The tubes were stood on a stand for 1 hour, and the grains well absorbed the water therein. With each tube opened, tubes with the sample grains were put in an electric rice cooker (Toshiba's RC-183, with 75 ml of deionized water put in the outer jacket), boiled for 15 minutes and then allowed to settle for 15 minutes therein to prepare boiled rice samples. DNA was extracted from each sample in the manner mentioned below.

Each one boiled rice grain was transferred to a microtube, to which was added 300 μl of tris-HCl buffer (100 mM, pH 8.0, containing 100 mM NaCl), and this was mashed with a pellet mixer. Next, 5 μl of heat-resistant amylase (α-amylase by Sigma, 790 U/mg solid, 1 mg/ml) was added to it, and reacted at 60° C. for 1 hour. Next, 5 μl of *Tritirachium album*-derived protease K (by Onko, 20 mg/ml) was added thereto, and reacted at 37° C. for 2 hours.

After the enzymatic reaction, 1 ml of ethanol cooled to −20° C. was added to each sample, and left at −20° C. for 15 minutes. Using a microcentrifuge, this was centrifuged (15000 G, 4° C., 15 minutes—the same shall apply hereinunder) to separate the precipitated residue. The residue was dissolved in 300 μl of TE (10 mM tris-HCl, pH 8.0, 1 mM EDTA), and 400 μl of phenol was added thereto. For DNA extraction, this was stirred in a rotary stirrer for 30 minutes.

Next, this was centrifuged to collect the supernatant, and PCI (phenol/chloroform/isoamyl alcohol, 25/24/1) of the same amount as that of the supernatant was added thereto. This was kept as it was for 30 minutes for DNA extraction, and then centrifuged to collect the supernatant. 6 ml of 5 M NaCl was added thereto, and 400 μl of cold ethanol was added thereto. Then, this was centrifuged, and the resulting precipitate was washed twice with 70% ethanol. The final precipitate was dissolved in 40 μl of 10-fold diluted TE to prepare a DNA sample solution. Its PCR was effected as follows:

The template DNA extracted from each boiled rice sample in the manner as above was amplified through PCR. The DNA polymerase used is Toyobo's Taq polymerase; and the PCR composition was prepared by mixing 10 μl of sterilized water, 0.2 μl of the polymerase, 2.5 μl of PCR buffer, 2.0 μl of $MgCl_2$, 3 μl of the template DNA and 1 μl of dNTPs (2.5 mM). The pair primers for PCR are S13F25 and S13R24 (SEQ ID Nos. 83 and 94) of 0.1 μl each; F6F25 and F6R22 (SEQ ID Nos. 43 and 44) of 0.2 μl each; A6F21 and A6R22 (SEQ ID Nos. 3 and 4) of 0.1 μl each; and P3F20 and P3R15 (SEQ ID Nos. 71 and 72) of 0.25 μl each. These pair primers were mixed with the PCR composition to be 20.0 μl in total.

The reactor is PCR Thermal Cycler MP (by Takara Bio Inc.) In the reactor, the template DNA was subjected to 45-cycle PCR. One PCR cycle comprises denaturation at 94° C. for 1 minute, annealing at 60° C. for 1 minute and chain-extension at 72° C. for 2 minutes. The amplified DNA was then subjected to electrophoresis and stained in the same manner as in Example 1. The PCR results are given in Table 6.

TABLE 6

Data of PCR with Four Primers Combined

| Variety | Primer | | | |
|---|---|---|---|---|
| | A6 | F6 | P3 | S13 |
| Koshihikari | − | − | + | − |
| Hitomebore | − | − | − | − |
| Hinohikari | − | − | + | − |
| Akitakomachi | − | − | − | − |
| Kirara 397 | − | − | + | + |
| Kinuhikari | + | − | + | − |
| Hoshinoyume | − | − | + | + |
| Haenuki | + | − | − | − |
| Mutsuhomare | − | + | − | − |
| Nipponbare | − | + | + | − |
| Sasanishiki | − | − | − | − |
| Tsugaruroman | − | + | − | − |
| Hanaechizen | − | − | + | − |
| Yumetsukushi | − | − | + | − |
| Hatsushimo | + | − | + | − |
| Asanohikari | − | − | + | − |
| Tsukinohikari | − | + | + | − |
| Aichinokaori | + | + | + | − |
| Matsuribare | − | + | + | − |
| Akiho | − | − | + | − |

+: Discrimination band appeared.
−: Discrimination band did not appear.

As in Table 6, the varieties that are negative to all the four primers tested with them are only three, "Hitomebore", "Akitakomachi" and "Sasanishiki". Therefore, when these three varieties are mixed with any of the other 17 varieties, the mixed rice can be surely detected as it is positive in the primary PCR.

Subsequently to the primary PCR in which the object varieties ("Hitomebore" and "Akitakomachi" in this case) are negative to all the primers used, each variety was subjected to secondary PCR. The secondary PCR is the same as the primary PCR except that the primers used in the former were WK9F20 and WK9R20 (SEQ ID Nos. 95 and 96) of 0.5 µl each; E30F28 and E30R24 (SEQ ID Nos. 39 and 40) of 0.05 µl each; G22F27 and G22R23 (SEQ ID Nos. 51 and 52) of 0.2 µl each; P5F20 and P5R25 (SEQ ID Nos. 75 and 76) of 0.3 µl each; and B43F17 and B43R18 (SEQ ID Nos. 27 and 28) of 0.25 µl each.

Figure 4:
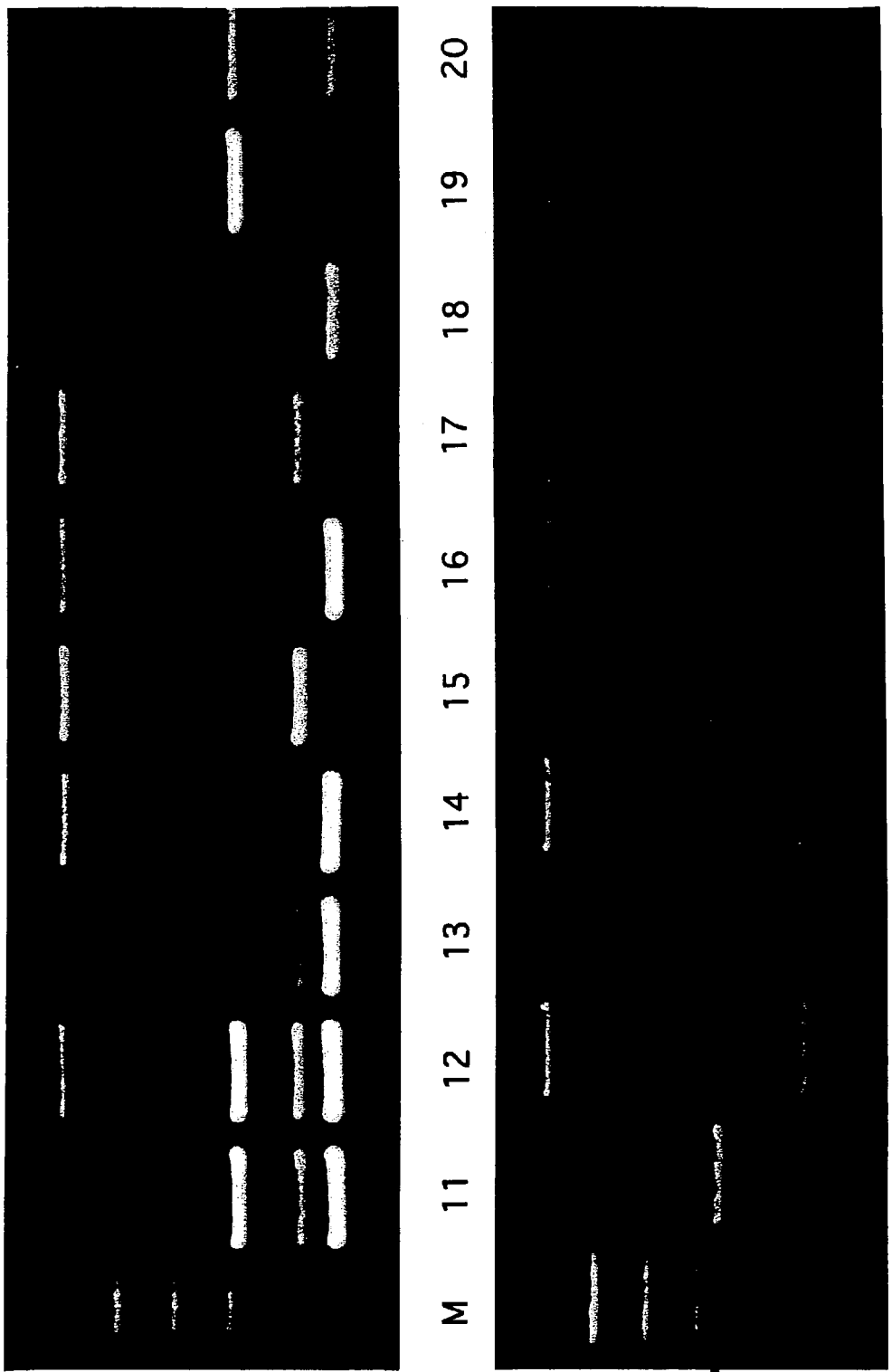
FIG. 4 shows migration photographs in electrophoresis after secondary PCR with five primers combined. In this, M indicates a molecular marker; lane 1 is "Koshihikari"; lane 2 is "Hitomebore"; lane 3 is "Hinohikari"; lane 4 is "Akitakomachi"; lane 5 is "Kirara 397"; lane 6 is "Kinuhikari"; lane 7 is "Hoshinoyume"; lane 8 is "Haenuki"; lane 9 is "Mutsuhomare"; lane 10 is "Nipponbare"; lane 11 is "Sasanishiki"; lane 12 is "Tsugaruroman"; lane 13 is "Hanaechizen"; lane 14 is "Yumetsukushi"; lane 15 is "Hatsushimo"; lane 16 is "Asanohikari"; lane 17 is "Tsukinohikari"; lane 18 is "Aichinokaori"; lane 19 is "Matsuribare"; lane 20 is "Akiho".

Each DNA amplified through the secondary PCR was subjected to electrophoresis and stained, and the results are shown in Table 7 and FIG. 4.

TABLE 7

Data of Secondary PCR with Five Primers Combined

| Variety | Primer | | | | |
|---|---|---|---|---|---|
| | WK9 | E30 | G22 | P5 | B43 |
| Koshihikari | − | − | + | + | + |
| Hitomebore | + | − | + | + | + |
| Hinohikari | + | − | + | + | − |
| Akitakomachi | + | − | − | + | − |
| Kirara 397 | + | − | + | − | − |
| Kinuhikari | + | − | − | + | − |
| Hoshinoyume | + | − | + | − | − |
| Haenuki | + | − | − | + | − |
| Mutsuhomare | − | − | − | + | + |
| Nipponbare | − | − | − | + | + |
| Sasanishiki | − | + | − | − | + |
| Tsugaruroman | + | − | − | + | − |
| Hanaechizen | + | − | − | + | − |
| Yumetsukushi | + | − | − | + | + |

TABLE 7-continued

Data of Secondary PCR with Five Primers Combined

| Variety | Primer | | | | |
|---|---|---|---|---|---|
| | WK9 | E30 | G22 | P5 | B43 |
| Hatsushimo | − | − | − | − | + |
| Asanohikari | + | − | − | − | − |
| Tsukinohikari | + | − | − | − | + |
| Aichinokaori | + | + | − | − | + |
| Matsuribare | + | − | + | − | − |
| Akiho | + | − | + | − | + |

+: Discrimination band appeared.
−: Discrimination band did not appear.

The secondary PCR results confirm that the three varieties "Hitomebore", "Akitakomachi" and "Sasanishiki" that were all negative in the primary PCR can be discriminated from each other.

In addition to the 17 varieties to which positive bands appeared in the primary PCR, comparing data in Table 6 with data in Table 7, it is suggested that all the best 20 varieties tested herein can be discriminated from each other through the process of this Example.

Accordingly, the presence or absence of mixed rice in the object variety "Hitomebore" or "Akitakomachi" can be detected through the primary PCR of 17 varieties except three varieties including the object varieties which appear negative band, and, in addition, the three varieties that are negative in the primary PCR can be discriminated from each other in the second PCR. Further, the 17 varieties that are all positive in the primary PCR can also be discriminated from each other on the basis of the results of the secondary PCR in which each one boiled rice grain of these varieties was tested.

Example 5

(Detection of Mixed Rice and Identification of the Varieties of the Mixed Rice by the use of Negative Band Groups Combined):

Best twenty varieties of rice harvested in 2000 in Japan, "Koshihikari", "Hitomebore", "Hinohikari", "Akitakomachi", "Kirara 397", "Kinuhikari", "Hoshinoyume", "Haenuki", "Mutsuhomare", "Nipponbare", "Sasanishiki", "Tsugaruroman", "Hanaechizen", "Yumetsukushi", "Hatsushimo", "Asanohikari", "Tsukinohikari", "Aichinokaori", "Matsuribare" and "Akiho" were tested, all unpolished. In the same manner as in Example 1, the rice samples were polished and ground, from which the genome DNA was extracted and subjected to PCR.

The PCR composition used herein was prepared by mixing 10 µl of sterilized water, 0.2 µl of polymerase (Taq polymerase (5U/µl) by Takara Bio Inc.), 2.5 µl of PCR buffer (12 mM tris-HCl, 60 mM KCl, pH 8.3), 2.0 µl of $MgCl_2$, 25 ng (1 µl) of the template DNA, and 1 µl of dNTPs (100 µM). For the oligonucleotide primers for PCR, prepared were a primer set of B43, G28, F6 and T16 for mixed rice detection in "Hinohikari", and a primer set of A6, E30, F6, G22 and P3 for mixed rice detection in "Akitakomachi". Concretely, pair primers B43F17 and B43R18 (SEQ ID Nos. 23 and 24) of 0.05 µl each; G28F17 and G28R28 (SEQ ID Nos. 47 and 48) of 0.4 µl each; F6F25 and F6R22 (SEQ ID Nos. 35 and 36) of 0.3 µl each; and T16F30 and F16R30 (SEQ ID Nos. 81 and 82) of 0.4 µl each were mixed with the PCR composition to be 17.85 µl in total, and pair primers A6F21 and A622R (SEQ ID Nos. 3 and 4) of 0.5 μl each; P3F20 and P3R15 (SEQ ID Nos. 71 and 72) of 2 μl each; E30F28 and E30R24 (SEQ ID Nos. 39 and 40) of 0.3 μl each; F6F25 and F6R22 (SEQ ID Nos. 43 and 44) of 0.3 μl each; and G22F27 and G22R23 (SEQ ID Nos. 51 and 52) of 0.3 μl each were mixed with the PCR composition to be 23.5 μl in total.

The reactor is PCR Thermal Cycler MP (by Takara Bio Inc.). In the reactor, the template DNA was subjected to 35-cycle PCR. One PCR cycle comprises denaturation at 94° C. for 1 minute, annealing at 61° C. for 1 minute and chain-extension at 72° C. for 2 minutes.

The amplified DNA was then subjected to electrophoresis and stained in the same manner as in Example 1. The test results are given in Table 8.

TABLE 8

Data of PCR with Primer Set for mixed rice detection in samples containing a small quantity of mixed rice

| | Primer | | | | | | | | |
|---|---|---|---|---|---|---|---|---|---|
| | Primer Set for mixed rice detection in "Hinohikari" | | | | Primer Set for mixed rice detection in "Akitakomachi" | | | | |
| Variety | B43 | G28 | F6 | T16 | A6 | E30 | F6 | G22 | P3 |
| Hinohikari | − | − | − | − | − | − | − | + | + |
| Akitakomachi | − | + | − | − | − | − | − | − | − |
| Koshihikari | + | + | − | − | − | − | − | + | + |
| Hitomebore | + | + | − | − | − | − | − | + | − |
| Kirara 397 | − | + | − | + | − | − | − | + | + |
| Kinuhikari | − | + | − | + | + | − | − | − | + |
| Hoshinoyume | − | + | − | − | − | − | − | + | + |
| Haenuki | − | + | − | − | + | − | − | − | − |
| Mutsuhomare | + | + | + | + | − | − | + | − | − |
| Nipponbare | + | − | + | − | − | − | + | − | + |
| Sasanishiki | + | − | − | − | − | + | − | + | − |
| Tsugaruroman | − | + | + | − | − | + | − | − | − |
| Hanaechizen | − | + | − | + | − | − | − | − | + |
| Yumetsukushi | + | + | − | − | − | − | − | − | + |
| Hatsushimo | + | − | − | + | + | − | − | − | + |
| Asanohikari | − | − | − | + | − | − | − | − | + |
| Tsukinohikari | + | − | + | + | − | − | + | − | + |
| Aichinokaori | + | − | + | + | + | + | + | − | + |
| Matsuribare | + | − | + | + | − | − | + | + | + |
| Akiho | + | − | − | + | − | − | − | + | + |

+: Discrimination band appeared.
−: Discrimination band did not appear.

The data in Table 8 confirm that using the DNA sets negative to both the object varieties "Hinohikari" and "Akitakomachi", which give no discrimination band for the object varieties but give discrimination bands for the other varieties specific thereto, enables the detection of mixed rice in the object varieties and enables the detection of mixed rice in all the best twenty varieties tested herein.

In addition, the PCR data in Table 8 in which 9 primers were used confirm that all the best twenty varieties tested can be discriminated from each other and further suggest that, when the mixed rice samples tested with the negative primer set gave a positive band, the variety of the mixed rice can be identified by extracting the DNA from each grain of the samples and subjecting the resulting template DNA to PCR with the nine primers used herein.

Example 6

(Detection of Variety Mixture in Barley and Identification of the Mixed Varieties):

Three varieties of barley, "Sanshu", "Ichibanboshi" and "Daikei HK64" were tested herein. Using a barley mill, these were milled into polished barley to a yield of 60%. Using an ultracentrifugal grinder (by Retsch), the polished barley samples were separately ground into powder samples.

A DNA was extracted from 6 g of each powder sample through CTAB treatment and purified in the same manner as in Example 1. This serves as a template DNA.

A PCR composition was prepared by mixing 0.2 μl of polymerase (Taq polymerase (5 U/μl) by Takara Bio Inc.), 2.5 μl of PCR buffer (12 mM tris-HCl, 60 mM KCl, pH 8.3), 2.0 μl of MgCl$_2$, 200 ng/1 μl of the template DNA, and 1 μl of dNTPs (100 μM). The pair primers for primary PCR are four, J6F18 and J6R20 (SEQ ID Nos. 59 and 60) of 0.6 μl each; A7F19 and A7R16 (SEQ ID Nos. 7 and 8) of 0.5 μl each; B7F22 and B7R17 (SEQ ID Nos. 19 and 20) of 0.5 μl each; and E30F28 and E30R24 (SEQ ID Nos. 39 and 40) of 0.4 μl each, and these were mixed with the PCR composition along with sterilized water to be 20.7 μl in total.

The pair primers for secondary PCR are four, G4F18 and G4R24 (SEQ ID Nos. 47 and 48) of 0.5 μl each; F6F25 and F6R22 (SEQ ID Nos. 43 and 44) of 0.5 μl each; M2CGF16 and M2CGR15 (SEQ ID Nos. 63 and 64) of 0.5 μl each; and WK9F20 and WK9R20 (SEQ ID Nos. 95 and 96) of 0.4 μl each, and these were mixed with the PCR composition along with sterilized water to be 20.7 μl in total.

The reactor is PCR Thermal Cycler MP (by Takara Bio Inc.) In the reactor, the template DNA was subjected to 35-cycle PCR. One PCR cycle comprises denaturation at 94° C. for 1 minute, annealing at 62° C. for 1 minute and chain-extension at 72° C. for 2 minutes. The amplified DNA was then subjected to electrophoresis in Mupid II (by Cosmobio), in which it was allowed to migrate in 2% agarose gel for 40 minutes, and stained with ethidium bromide to give a band pattern through exposure to UV light. The test results are given in Table 9.

In the primary PCR for detection of variety mixture in barley, only "Ichibanboshi" gave no discrimination band with all the four pair primers used, but "Sanshu" and "Daikei HK64" gave a discrimination band with the primer J6. This means that these varieties "Sanshu" and "Daikei HK64" mixed in the other variety "Ichibanboshi" can be detected through the primary PCR.

In the secondary PCR for identifying the mixed varieties, "Sanshu" was negative to all the primers tested with it, but "Ichibanboshi" gave a discrimination band with M2CG and "Daikei HK64" also gave a discrimination band with G4 and M2CG. Combining the results of the primary PCR with those of the secondary PCR makes it possible to identify the mixed varieties "Sanshu" and "Daikei HK64" from each other.

TABLE 9

Results of PCR for detecting variety mixture in barley and identifying the mixed varieties

| | Primary PCR for detecting variety mixture | | | |
|---|---|---|---|---|
| | Primer | | | |
| Variety | J6 | A7 | E30 | B7 |
| Ichibanboshi | − | − | − | − |
| Sanshu | + | − | − | − |
| Daikei HK64 | + | − | − | − |

TABLE 9-continued

Results of PCR for detecting variety mixture in barley and identifying the mixed varieties

| Variety | G4 | F6 | M2CG | WK9 |
|---|---|---|---|---|
| Secondary PCR for identifying mixed varieties | | | | |
| | | Primer | | |
| Ichibanboshi | − | − | + | − |
| Sanshu | − | − | − | − |
| Daikei HK64 | + | − | + | − |

+: Discrimination band appeared.
−: Discrimination band did not appear.

Example 7

(Detection of Variety Mixture in Corn and Identification of the Mixed Varieties):

Three varieties of corn, "Petercorn", "Honeybantam" and "Waxycorn" were tested herein. Using a freeze-drier, Aira's FD200, these were freeze-dried. Using a mill, Iwatani's Coffee Millcer, the freeze-dried samples were separately ground into powder samples. A DNA was extracted from 6 g of each powder sample through CTAB treatment and purified in the same manner as in Example 1. This serves as a template DNA.

A PCR composition was prepared by mixing 11.74 µl of sterilized water, 0.2 µl of polymerase (Taq polymerase (5 U/µl) by Takara Bio Inc.), 2.5 µl of PCR buffer (12 mM tris-HCl, 60 mM KCl, pH 8.3), 2.0 µl of MgCl$_2$, 200 ng/1 µl of the template DNA, and 1 µl of dNTPs (100 µM). The pair primers for primary PCR are four, A7F19 and A7R16 (SEQ ID Nos. 7 and 8) of 0.6 µl each; E30F28 and E30R24 (SEQ ID Nos. 39 and 40) of 0.5 µl each; F6F25 and F6R22 (SEQ ID Nos. 43 and 44) of 0.5 µl each; and S13F25 and S13R24 (SEQ ID Nos. 83 and 84) of 0.4 µl each. These were mixed with the PCR composition to be 22.44 µl in total.

The pair primers for secondary PCR are four, A6F21 and A6R22 (SEQ ID Nos. 3 and 4) of 0.5 µl each; G4F18 and G4R24 (SEQ ID Nos. 47 and 48) of 0.5 µl each; J6F18 and J6R20 (SEQ ID Nos. 59 and 60) of 0.4 µl each; and M2CGF16 and M2CGR15 (SEQ ID Nos. 63 and 64) of 0.3 µl each. These were mixed with the PCR composition to be 20.7 µl in total.

The reactor is a temperature-controlled system PC700 (by Astec). In the reactor, the template DNA was subjected to 35-cycle PCR. One PCR cycle comprises denaturation at 94° C. for 1 minute, annealing at 62° C. for 1 minute and chain-extension at 72° C. for 2 minutes. The amplified DNA was then subjected to electrophoresis in Mupid II (by Cosmobio), in which it was allowed to migrate in 2% agarose gel for 40 minutes, and stained with ethidium bromide to give a band pattern through exposure to UV light. The test results are given in Table 10.

TABLE 10

Results of two-step PCR for detecting variety mixture in corn and identifying the mixed varieties Primary PCR for detecting variety mixture

| | Primer | | | |
|---|---|---|---|---|
| Variety | A7 | E30 | F6 | S13 |
| Honeybantam | − | − | − | − |
| Petercorn | − | − | − | − |
| Waxycorn | + | + | + | + |

Secondary PCR for identifying mixed varieties

| | Primer | | | |
|---|---|---|---|---|
| Variety | A6 | G4 | J6 | M2CG |
| Honeybantam | + | − | − | + |
| Petercorn | − | − | + | − |
| Waxycorn | + | + | + | + |

+: Discrimination band appeared.
−: Discrimination band did not appear.

In the primary PCR for detection of variety mixture in corn, "Honeybantam" and "Petercorn" gave no discrimination band with all the four pair primers used, but "Waxycorn" gave a discrimination band with the primers A7, E30, F6 and S13. This means that the variety "Waxycorn" mixed in "Honeybantam" or "Petercorn" can be detected through the primary PCR.

In the secondary PCR for identifying the mixed varieties, "Honeybantam" gave a discrimination band with A6 and M2CG; "Petercorn" gave a discrimination band with J6; and "Waxycorn" gave a discrimination band with A6, G4, J6 and M2CG. Combining the results of the primary PCR with those of the secondary PCR makes it possible to discriminate these three varieties from each other.

Example 8

(Definition of the Range of Primer Length):

Two varieties of unpolished rice, "Koshihikari" and "Hoshinoyume" were tested.

Using a laboratory rice mill, (Yamamoto Seisakusho's Ricepal VP31T), these were milled into polished rice to a yield of 90%. Using an ultracentrifugal grinder (by Retsch), the polished rice samples were separately ground. A genome DNA was extracted from 6 g of each powder sample processed with CTAB. Samples of the genome DNA for PCR were prepared, each having a DNA concentration of about 400 µg/ml measured through UV absorptiometry (at 260 nm).

Three different types of oligonucleotide primers were prepared for PCR. One is a pair of long primers, SEQ ID Nos. 97 and 98 each having 40 base residues; another is a pair primer of SEQ ID Nos. 83 (25-mer) and 84 (24-mer); and still another is a pair primer of SEQ ID Nos. 99 (12-mer) and 100 (12-mer) These three types of pair primers were separately used in PCR.

The DNA polymerase is a Taq polymaraze (5 U/µl, by Toyobo). The PCR composition was prepared by mixing 10 µl of sterilized water, 0.2 µl of the polymerase, 2.5 µl of PCR buffer, 2.0 µl of MgCl$_2$, 3 µl of the template DNA, and 1.0 µl of dNTPs (2.5 mM). The pair primers of 1.0 µl each (totaling 2.0 µl) were mixed with the PCR composition to be 20.7 µl in total.

The reactor is PCR Thermal Cycler MP (by Takara Bio Inc.) In the reactor, the template DNA was subjected to 45-cycle PCR. One PCR cycle comprises denaturation at 94° C. for 1 minute, annealing at 38° C. for 1 minute and chain-extension at 72° C. for 2 minutes.

The amplified DNA was then subjected to electrophoresis in Mupid II (by Cosmobio), in which it was allowed to migrate in 2% agarose gel for 40 minutes, and stained with ethidium bromide to give a band pattern through exposure to UV light. The results were as follows: The PCR system with the pair of long primers of 40 base residues each gave no band; and that with the pair of short primers of 12 base residues each gave a large number of bands. Accordingly, the two systems are unfavorable to the present invention which is for accurately discriminating grain varieties from each other.

As opposed to these, the PCR system with the pair of 25-mer and 24-mer primers gave a discrimination band of 1.8 kbp for "Hoshinoyume" but gave no discrimination band for "Koshihikari". This means that the pair primers are useful in grain variety discrimination.

Example 9

(Identification of Different Varieties in Boiled Samples of Imported Rice):

Seven varieties of rice, "Koshihikari" (in Japan) "Ippin" (from Korea), "Bannishiki" (from China), "Amaroo" (from Australia), "Tamaki" (from USA), "Kaodocumari 105" (from Thailand), and "Motoboi" (from Vietnam) were tested, all unpolished. Using Pearlest (by Kett Scientific Laboratories), these samples of 10 g each were milled into polished rice to a yield of 90%. One grain of each polished rice sample was put into a plastic tube (by Assist, 1.5 ml volume), and 35 μl of deionized water was added thereto. The tubes were stood on a stand for 1 hour, and the grains well absorbed the water therein. With each tube opened, those tubes with the sample grains were put in an electric rice cooker (Toshiba's RC-183, with 75 ml of deionized water put in the outer jacket), boiled for 15 minutes and then allowed to settle for 15 minutes therein to prepare boiled rice samples. DNA was extracted from each sample in the manner mentioned below.

Each one boiled rice grain was put in a microtube, to which was added 300 μμl of tris-HCl buffer (100 mM, pH 8.0, containing 100 mM NaCl), and this was mashed in a pellet mixer. Next, 5 μl of heat-resistant amylase (α-amylase by Sigma, 790 U/mg solid, 1 mg/ml) was added to it, and reacted at 60° C. for 1 hour. Next, 5 μl of Tritirachium album-derived protease K (by Onko, 20 mg/ml) was added thereto, and reacted at 37° C. for 2 hours.

After the enzymatic reaction, 1 ml of ethanol cooled to −20° C. was added to each sample, and left at −20° C. for 15 minutes. Using a microcentrifuge, this was centrifuged (15000 G, 4° C., 15 minutes—the same shall apply hereinunder) to separate the precipitated residue. The residue was dissolved in 300 μl of TE (10 mM tris-HCl, pH 8.0, 1 mM EDTA), and 400 μl of phenol was added thereto. For DNA extraction, this was stirred in a rotary stirrer for 30 minutes.

Next, this was centrifuged to collect the supernatant, and PCI (phenol/chloroform/isoamyl alcohol, 25/24/1) of the same amount as that of the supernatant was added thereto. This was kept as it was for 30 minutes for DNA extraction, and then centrifuged to collect the supernatant. 6 ml of 5 M NaCl was added thereto, and 400 μl of cold ethanol was thereto. Then, this was centrifuged, and the resulting precipitate was washed twice with 70% ethanol. The final precipitate was dissolved in 40 μl of 10-fold diluted TE to prepare a DNA sample solution.

This was subjected to PCR, as follows:

The template DNA extracted from each boiled rice sample in the manner as above was amplified. The DNA polymerase used is Toyobo's Taq polymerase; and the PCR composition was prepared by mixing 10 μl of sterilized water, 0.2 μl of the polymerase, 2.5 μl of PCR buffer, 2.0 μl of $MgCl_2$, 3 μl of the template DNA and 1.0 μl of dNTPs (2.5 mM). The pair primers for PCR are WK9F20 and WK9R20 (SEQ ID Nos. 95 and 96) of 0.25 μl each; A7F19 and A7R16 (SEQ ID Nos. 7 and 8) of 0.25 μl each; S13F25 and S13R24 (SEQ ID Nos. 83 and 84) of 0.25 μl each; and J6F18 and J6R20 (SEQ ID Nos. 59 and 60) of 0.25 μl each. These pair primers were mixed with the PCR composition to be 20.7 μl in total.

The reactor is PCR Thermal Cycler MP (by Takara Bio Inc.) In the reactor, the template DNA was subjected to 45-cycle PCR. One PCR cycle comprises denaturation at 94° C. for 1 minute, annealing at 60° C. for 1 minute and chain-extension at 72° C. for 2 minutes.

The amplified DNA was then subjected to electrophoresis in the same manner as in Example 1. The PCR data of the template DNAs extracted from the seven varieties are given in Table 11.

The data in this Table confirm that the method of the present invention is applicable also to boiled samples of imported rice. When two pair primers WK9 and S13 only were used, "Koshihikari" could be discriminated with all 6 imported rices. But the two varieties "Bannishiki" and "Motoboi" could not be discriminated from each other, and the three varieties "Amaroo", "Tamaki" and "Kaodocumari 105" could not either. However, when these two pair primers were combined with the other two pair primers A7 and J6, the former two varieties and also the latter three varieties were all discriminated from each other. This means that mixing of imported rice to "Koshihikari" can be easily detected by the use of former two primers. And all the seven varieties tested herein can be discriminated from each other through PCR with the combined four pair primers.

TABLE 11

Data of PCR of boiled rice of seven varieties with four pair primers combined

| Variety | Primer | | | |
|---|---|---|---|---|
| | WK9 | S13 | A7 | J6 |
| Koshihikari (Japan) | − | − | + | + |
| Ippin (Korea) | + | − | + | − |
| Bannishiki (China) | + | + | + | + |
| Amaroo (Australia) | − | + | + | + |
| Tamaki (USA) | − | + | − | + |

TABLE 11-continued

Data of PCR of boiled rice of seven varieties with four pair primers combined

| Variety | Primer | | | |
|---|---|---|---|---|
| | WK9 | S13 | A7 | J6 |
| Kaodocumari 105 | − | + | − | − |
| Motoboi | (Thailand) | (Vietnam) | + | + | − |

Example 10

(Usefulness of other Primer Groups):

Unpolished rice samples of "Koshihikari", "Hinohikari", "Akitakomachi", "Kinuhikari", "Haenuki", "Nipponbare" and "Sasanishiki" were tested in the same process of PCR and electrophoresis as in Example 1, for which, however, the pair primers used are B1F25 and B1R20 (SEQ ID Nos. 15 and 16); E22F20 and E22R21 (SEQ ID Nos. 35 and 36); Q16F25 and Q16R20 (SEQ ID Nos. 79 and 80); T8F22 and T8R25 (SEQ ID Nos. 87 and 88); and B18F15 and B18R21 (SEQ ID Nos. 23 and 24). The test results are given in Table 12.

The results in this Table confirm that the pair primers used herein make it possible to discriminate all these seven varieties from each other.

TABLE 12

Data of PCR of 7 rice varieties with various types of pair primers

| Variety | Primer | | | | |
|---|---|---|---|---|---|
| | B1 | E22 | Q16 | T8 | B18 |
| Koshihikari | − | + | + | − | + |
| Hinohikari | + | − | + | − | + |
| Akitakomachi | − | + | + | + | + |
| Kinuhikari | + | + | + | + | + |
| Haenuki | − | + | + | − | − |
| Nipponbare | + | − | − | − | − |
| Sasanishiki | − | − | + | + | − |

What is claimed is:

1. A method of identifying the grain varieties contained in a sample containing one or more unidentified grain varieties comprising:

extracting DNA from the grain varieties contained in said sample;

selectively amplifying said DNA by conducting multiplex PCR using the following primer pairs: SEQ ID NOs: 3 and 4; SEQ ID NOs: 19 and 20; SEQ ID NOs: 43 and 44; and SEQ ID NOs: 95 and 96;

detecting absence or presences of bands corresponding to the amplification product for each of said primer pairs; and comparing the pattern of bands obtained from said detecting with the pattern of bands determined for a sample containing a known grain variety determined by selectively amplifying DNA obtained by multiplex PCR using the primer pairs: SEQ ID NOs: 3 and 4; SEQ ID NOs: 19 and 20; SEQ ID NOs: 43 and 44; and SEQ ID NOs: 95 and 96 thereby identifying the grain varieties contained in said sample.

2. The method of claim 1, further comprising further refining the identification of the grain varieties in the sample by further subjecting the sample to secondary multiplex PCR.

3. The method of claim 1, wherein the grain varieties are any of rice, wheat, corn or barley.

4. The method of claim 2, wherein the grain varieties are any of rice, wheat, corn or barley.

5. The method of claim 3, wherein the method is a method of detecting the presence or absence of a specific object variety of rice wherein said object variety of rice is a variety of high-quality rice.

6. The method of claim 4, wherein the method is a method of detecting the presence or absence of a specific object variety of rice wherein said object variety of rice is a variety of high-quality rice.

7. The method of claim 5, wherein the high-quality rice is any of "Koshihikari", "Hitomebore", "Akitakomachi" or "Hinohikari".

8. The method of claim 6, wherein the high-quality rice is any of "Koshihikari", "Hitomebore", "Akitakomachi" or "Hinohikari".

9. The method of claim 2, wherein secondary multiplex PCR is conducted using two or more primer pairs wherein each primer pair contains two primers and each primer is composed of from 13 to 29 bases and prepared by deleting 1 to 17 bases from the 3' side of the nucleic acid sequence defined as being present in said primer pair, wherein said primer pairs are selected from the group consisting of SEQ ID NOs: 5 and 6; SEQ ID NOs: 9 and 10; SEQ ID NOs: 13 and 14; SEQ ID NOs: 21 and 22; SEQ ID NOs: 25 and 26; SEQ ID NOs: 29 and 30; SEQ ID NOs: 33 and 34; SEQ ID NOs: 37 and 38; SEQ ID NOs: 45 and 46; SEQ ID NOs: 49 and 50; SEQ ID NOs: 53 and 54; SEQ ID NOs: 57 and 58; SEQ ID NOs: 61 and 62; SEQ ID NOs: 65 and 66; SEQ ID NOs: 69 and 70; SEQ ID NOs: 73 and 74; SEQ ID NOs: 77 and 78; SEQ ID NOs: 81 and 82; SEQ ID NOs: 85 and 86; and SEQ ID NOs: 89 and 90.

10. The method of claim 2, wherein secondary multiplex PCR is conducted using two or more primer pairs selected from the group consisting of SEQ ID NOs: 7 and 8; SEQ ID NOs: 11 and 12; SEQ ID NOs: 15 and 16; SEQ ID NOs: 23 and 24; SEQ ID NOs: 27 and 28; SEQ ID NOs: 31 and 32; SEQ ID NOs: 35 and 36; SEQ ID NOs: 39 and 40; SEQ ID NOs: 47 and 48; SEQ ID NOs: 51 and 52; SEQ ID NOs: 55 and 56; SEQ ID NOs: 59 and 60; SEQ ID NOs: 63 and 64; SEQ ID NOs: 67 and 68; SEQ ID NOs: 71 and 72; SEQ ID NOs: 75 and 76; SEQ ID NOs: 79 and 80; SEQ ID NOs: 83 and 84; SEQ ID NOs: 87 and 88; and SEQ ID NOs: 91 and 92.

11. The method of claim 5, wherein the high-quality rice is "Koshihikari", and the multiplex PCR uses a primer set of four primer pairs SEQ ID NOs: 27 and 28; SEQ ID NOs: 51 and 52; SEQ ID NOs: 67 and 68; and SEQ ID NOs: 95 and 96, and/or a primer set of at least three primer pairs selected from the group consisting of SEQ ID NOs: 3 and 4; SEQ ID NOs: 19 and 20; SEQ ID NOs: 39 and 40; SEQ ID NOs: 43 and 44; SEQ ID NOs: 47 and 48; SEQ ID NOs: 63 and 64; SEQ ID NOs: 83 and 84; SEQ ID NOs: 87 and 88; SEQ ID NOs: 91 and 92; and SEQ ID NOs: 95 and 96.

12. The method of claim 5, wherein the high-quality rice is "Hitomebore", and the multiplex PCR uses a primer pair set of at least three primer pairs selected from the group consisting of SEQ ID NOs: 3 and 4; SEQ ID NOs: 19 and 20; SEQ ID NOs: 43 and 44; SEQ ID NOs: 47 and 48; SEQ ID NOs: 71 and 72; SEQ ID NOs: 83 and 84; SEQ ID NOs: 87 and 88; and SEQ ID NOs: 91 and 92, and/or a primer set of five primer pairs SEQ ID NOs: 19 and 20; SEQ ID NOs: 47 and 48; SEQ ID NOs: 51 and 52; SEQ ID NOs: 75 and 76; and SEQ ID NOs: 95 and 96.

13. The method of claim 5, wherein the high-quality rice is "Akitakomachi", and the multiplex PCR uses a primer pair set of at least three primer pairs selected from the group consisting of SEQ ID NOs: 3 and 4; SEQ ID NOs: 19 and 20; SEQ ID NOs: 39 and 40; SEQ ID NOs: 43 and 44; SEQ ID NOs: 47 and 48; SEQ ID NOs: 51 and 52; SEQ ID NOs: 63 and 64; SEQ ID NOs: 71 and 72; SEQ ID NOs: 83 and 84; and SEQ ID NOs: 91 and 92, and/or a primer set of four primer pairs SEQ ID NOs: 3 and 4; SEQ ID NOs: 19 and 20; SEQ ID NOs: 63 and 64; and SEQ ID NOs: 71 and 72, or four primer pairs SEQ ID NOs: 95 and 96; SEQ ID NOs: 27 and 28; SEQ ID NOs: 67 and 68; and SEQ ID NOs: 51 and 52.

14. The method of claim 5, wherein the high-quality rice is "Hinohikari", and the multiplex PCR uses a primer pair set of at least three primer pairs selected from the group consisting of SEQ ID NOs: 3 and 4; SEQ ID NOs: 19 and 20; SEQ ID NOs: 27 and 28; SEQ ID NOs: 35 and 36; SEQ ID NOs: 39 and 40; SEQ ID NOs: 43 and 44; SEQ ID NOs: 47 and 48; SEQ ID NOs: 55 and 56; SEQ ID NOs: 83 and 84; SEQ ID NOs: 87 and 88; and SEQ ID NOs: 91 and 92, and/or a primer set of four primers-SEQ ID NOs: 27 and 28; SEQ ID NOs: 43 and 44; SEQ ID NOs: 55 and 56; and SEQ ID NOs: 91 and 92, or five pair primers SEQ ID NOs: 27 and 28; SEQ ID NOs: 51 and 52; SEQ ID NOs: 55 and 56; SEQ ID NOs: 75 and 76; and SEQ ID NOs: 95 and 96.

15. The method of claim 1, wherein the sample is boiled rice.

16. The method of claim 1, wherein every one grain of the sample is individually inspected.

17. The method of claim 2, wherein the sample is boiled rice.

18. The method of claim 2, wherein every one grain of the sample is individually inspected.

19. The method of claim 3, wherein the sample is boiled rice.

20. The method of claim 3, wherein every one grain of the sample is individually inspected.

21. The method of claim 4, wherein the sample is boiled rice.

22. The method of claim 4, wherein every one grain of the sample is individually inspected.

23. The method of claim 5, wherein the sample is boiled rice.

24. The method of claim 5, wherein every one grain of the sample is individually inspected.

25. The method of claim 6, wherein the sample is boiled rice.

26. The method of claim 6, wherein every one grain of the sample is individually inspected.

27. The method of claim 7, wherein the sample is boiled rice.

28. The method of claim 7, wherein every one grain of the sample is individually inspected.

29. The method of claim 8, wherein the sample is boiled rice.

30. The method of claim 8, wherein every one grain of the sample is individually inspected.

31. The method of claim 9, wherein the sample is boiled rice.

32. The method of claim 9, wherein every one grain of the sample is individually inspected.

33. The method of claim 10, wherein the sample is boiled rice.

34. The method of claim 10, wherein every one grain of the sample is individually inspected.

35. The method of claim 11, wherein the sample is boiled rice.

36. The method of claim 11, wherein every one grain of the sample is individually inspected.

37. The method of claim 12, wherein the sample is boiled rice.

38. The method of claim 12, wherein every one grain of the sample is individually inspected.

39. The method of claim 13, wherein the sample is boiled rice.

40. The method of claim 13, wherein every one grain of the sample is individually inspected.

41. The method of claim 14, wherein the sample is boiled rice.

42. The method of claim 14, wherein every one grain of the sample is individually inspected.

* * * * *

UNITED STATES PATENT AND TRADEMARK OFFICE
CERTIFICATE OF CORRECTION

| | |
|---|---|
| PATENT NO. | : 7,041,452 B2 |
| APPLICATION NO. | : 10/217106 |
| DATED | : May 9, 2006 |
| INVENTOR(S) | : Ohtsubo et al. |

Page 1 of 1

It is certified that error appears in the above-identified patent and that said Letters Patent is hereby corrected as shown below:

On the title page, Item (54) and top of column 1, the title is incorrect. Item (54) and top of column 1 should read:
-- METHOD OF DETECTING THE PRESENCE OR ABSENCE OF MIXED VARIETIES IN GRAINS, AND IDENTIFYING THE MIXED VARIETIES --

Signed and Sealed this

Fourteenth Day of November, 2006

JON W. DUDAS
*Director of the United States Patent and Trademark Office*

```
                         SEQUENCE LISTING

<160> NUMBER OF SEQ ID NOS: 100

<210> SEQ ID NO 1
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
ccagctgaac gcctgtacta caagaattaa                                    30

<210> SEQ ID NO 2
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
ccagctgtac gtcttcccca gcgccggcgg                                    30

<210> SEQ ID NO 3
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
ccagctgtac gcctgtacta c                                             21

<210> SEQ ID NO 4
<211> LENGTH: 22
<212> TYPE: DNA
<213> ORGANISM: ARTIFICIAL SEQUENCE
```

-continued

```
<220> FEATURE:
<223> OTHER INFORMATION: SYNTHETIC DNA

<400> SEQUENCE: 4
ccagctgtac gtcttcccca gc                                          22

<210> SEQ ID NO 5
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
tgcctcgcac cagaaatagt ataatcccaa                                  30

<210> SEQ ID NO 6
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
tgcctcgcac catgaggtgt ggccgagtac                                  30

<210> SEQ ID NO 7
<211> LENGTH: 19
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
tgcctcgcac cagaaatag                                              19

<210> SEQ ID NO 8
<211> LENGTH: 16
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
tgcctcgcac catgag                                                 16

<210> SEQ ID NO 9
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
cttgtcatgt gtttatcatt tgactattta                                  30

<210> SEQ ID NO 10
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
cttgtcatgt gtagtgcggc ttgttttctg                                  30
```

<210> SEQ ID NO 11
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
cttgtcatgt gtttatcatt tgactattta                            30

<210> SEQ ID NO 12
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
cttgtcatgt gtagtccggc t                                     21

<210> SEQ ID NO 13
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
gtttcgctcc tacagtaatt aaggggctat                            30

<210> SEQ ID NO 14
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 14
gtttcgctcc catgcaatct gcaaaagttt                            30

<210> SEQ ID NO 15
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
gtttcgctcc tacagtaatt aaggg                                 25

<210> SEQ ID NO 16
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 16
gtttcgctcc catgcaatct                                       20

<210> SEQ ID NO 17
<211> LENGTH: 30
<212> TYPE: DNA
<213> ORGANISM: ARTIFICIAL SEQUENCE
<220> FEATURE:
<223> OTHER INFORMATION: SYNTHETIC DNA

```
<400> SEQUENCE: 17
caggtgtggg ttacaaggat gacccttggg                                    30

<210> SEQ ID NO 18
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
caggtgtggg ttcacggcct tgattaataa                                    30

<210> SEQ ID NO 19
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 19
caggtgtggg ttacaaggat ga                                            22

<210> SEQ ID NO 20
<211> LENGTH: 17
<212> TYPE: DNA
<213> ORGANISM: ARTIFICIAL SEQUENCE
<220> FEATURE:
<223> OTHER INFORMATION: SYNTHETIC DNA

<400> SEQUENCE: 20
caggtgtggg ttcacgg                                                  17

<210> SEQ ID NO 21
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 21
ccacagcagt gcttcatgtc atgtagaata                                    30

<210> SEQ ID NO 22
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 22
ccacagcagt tcaaatacac caggaatttc                                    30

<210> SEQ ID NO 23
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 23
ccacagcagt gcttc                                                    15

<210> SEQ ID NO 24
```

```
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 24
ccacagcagt gcttcatgtc a                                           21

<210> SEQ ID NO 25
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 25
tggccggcat gactcacata cccaacatat                                  30

<210> SEQ ID NO 26
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 26
actggccggc atcaagacca accaatttgg                                  30

<210> SEQ ID NO 27
<211> LENGTH: 17
<212> TYPE: DNA
<213> ORGANISM: ARTIFICIAL SEQUENCE
<220> FEATURE:
<223> OTHER INFORMATION: SYNTHETIC DNA

<400> SEQUENCE: 27
tggccggcat gactcac                                                17

<210> SEQ ID NO 28
<211> LENGTH: 18
<212> TYPE: DNA
<213> ORGANISM: ARTIFICIAL SEQUENCE
<220> FEATURE:
<223> OTHER INFORMATION: SYNTHETIC DNA

<400> SEQUENCE: 28
actggccggc atcaagac                                               18

<210> SEQ ID NO 29
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 29
gtggatctga attcactcaa ctatttgtac                                  30

<210> SEQ ID NO 30
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 30
```
gtggatctga atcacagatg acattatagg          30

<210> SEQ ID NO 31
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 31
gtggatctga attcactcaa cta                 23

<210> SEQ ID NO 32
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 32
gtggatctga atcacagatg a                   21

<210> SEQ ID NO 33
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 33
ggaatggaac cgaagtggag ctattccctg          30

<210> SEQ ID NO 34
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 34
ggaatggaac cgccgtaaac ttgaatgcta          30

<210> SEQ ID NO 35
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 35
ggaatggaac cgaagtggag                     20

<210> SEQ ID NO 36
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 36
ggaatggaac cgccgtaaac t                   21

<210> SEQ ID NO 37
<211> LENGTH: 30
<212> TYPE: DNA

```
<213> ORGANISM: ARTIFICIAL SEQUENCE
<220> FEATURE:
<223> OTHER INFORMATION: SYNTHETIC DNA

<400> SEQUENCE: 37
tacctggttg atgtatacag atctggttat                                30

<210> SEQ ID NO 38
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 38
atccctcgat ccctctagca ttatatcctc                                30

<210> SEQ ID NO 39
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 39
tacctggttg atgtatacag atctggtt                                  28

<210> SEQ ID NO 40
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 40
atccctcgat ccctctagca ttat                                      24

<210> SEQ ID NO 41
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 41
accactccat atatatcatc caaagttcta                                30

<210> SEQ ID NO 42
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 42
accactccat atcaccacaa ggcgtttagg                                30

<210> SEQ ID NO 43
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 43
accactccat atatatcatc caaag                                     25
```

<210> SEQ ID NO 44
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 44
accactccat atcaccacaa gg                                    22

<210> SEQ ID NO 45
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 45
gagaccgata tgcgattcgc ggcattggac                            30

<210> SEQ ID NO 46
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 46
gtggtgttta gatccagaga cttaacttta                            30

<210> SEQ ID NO 47
<211> LENGTH: 18
<212> TYPE: DNA
<213> ORGANISM: ARTIFICIAL SEQUENCE
<220> FEATURE:
<223> OTHER INFORMATION: SYNTHETIC DNA

<400> SEQUENCE: 47
gagaccgata tgcgattc                                         18

<210> SEQ ID NO 48
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 48
gtggtgttta gatccagaga ctta                                  24

<210> SEQ ID NO 49
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 49
ctcactcaaa tttacagtgc attttcttgt                            30

<210> SEQ ID NO 50
<211> LENGTH: 30
<212> TYPE: DNA
<213> ORGANISM: ARTIFICIAL SEQUENCE
<220> FEATURE:

<223> OTHER INFORMATION: SYNTHETIC DNA

<400> SEQUENCE: 50
agggccatga tacaagactc tgttctgtag                              30

<210> SEQ ID NO 51
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 51
ctcactcaaa tttacagtgc attttct                                 27

<210> SEQ ID NO 52
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 52
agggccatga tacaagactc tgt                                     23

<210> SEQ ID NO 53
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 53
ggccgtcgtt ctgcgatggt ctccaagaat                              30

<210> SEQ ID NO 54
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 54
ggagaatccc acagtaagtt tttctttgtt                              30

<210> SEQ ID NO 55
<211> LENGTH: 17
<212> TYPE: DNA
<213> ORGANISM: ARTIFICIAL SEQUENCE
<220> FEATURE:
<223> OTHER INFORMATION: SYNTHETIC DNA

<400> SEQUENCE: 55
ggcggtcgtt ctgcgat                                            17

<210> SEQ ID NO 56
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 56
ggagaatccc acagtaagtt tttctttg                                28

<210> SEQ ID NO 57
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 57
gtcggagtgg tcagaccggg ctagcttttg            30

<210> SEQ ID NO 58
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 58
gtcggagtgg atggagtagc ggtgggtgtg            30

<210> SEQ ID NO 59
<211> LENGTH: 18
<212> TYPE: DNA
<213> ORGANISM: ARTIFICIAL SEQUENCE
<220> FEATURE:
<223> OTHER INFORMATION: SYNTHETIC DNA

<400> SEQUENCE: 59
gtcggagtgg tcagaccg                         18

<210> SEQ ID NO 60
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 60
gtcggagtgg atggagtagc                       20

<210> SEQ ID NO 61
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 61
acaacgcctc cgatgatcga accatatctt            30

<210> SEQ ID NO 62
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 62
acaacgcctc cgacaacaag attttctcct            30

<210> SEQ ID NO 63
<211> LENGTH: 16
<212> TYPE: DNA
<213> ORGANISM: ARTIFICIAL SEQUENCE
<220> FEATURE:
<223> OTHER INFORMATION: SYNTHETIC DNA

```
<400> SEQUENCE: 63
acaacgcctc cgatga                                                    16

<210> SEQ ID NO 64
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 64
acaacgcctc cgaca                                                     15

<210> SEQ ID NO 65
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 65
gtccactgtg accacaacat ttcttccagc                                     30

<210> SEQ ID NO 66
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 66
gtccactgtg gggattgttc cataaaagat                                     30

<210> SEQ ID NO 67
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 67
gtccactgtg accacaacat                                                20

<210> SEQ ID NO 68
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 68
gtccactgtg gggattgttt                                                20

<210> SEQ ID NO 69
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 69
aacgggccaa aaacggaggt cgtatggagc                                     30

<210> SEQ ID NO 70
<211> LENGTH: 30
```

```
<212> TYPE: DNA
<213> ORGANISM: ARTIFICIAL SEQUENCE
<220> FEATURE:
<223> OTHER INFORMATION: SYNTHETIC DNA

<400> SEQUENCE: 70
aacgggccaa cgcagccatt aaagagaaat                                        30

<210> SEQ ID NO 71
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 71
aacgggccaa aaacggaggt                                                   20

<210> SEQ ID NO 72
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 72
aacgggccaa cgcag                                                        15

<210> SEQ ID NO 73
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 73
acaacggtcc gtccttgctt aggaaaaggc                                        30

<210> SEQ ID NO 74
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 74
acaacggtcc aacagatact tttgaaaaac                                        30

<210> SEQ ID NO 75
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 75
acaacggtcc gtccttgctt                                                   20

<210> SEQ ID NO 76
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 76
```
acaacggtcc aacagatact tttga    25

<210> SEQ ID NO 77
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 77
agtgcagcca ttatatagga ctaacaagga    30

<210> SEQ ID NO 78
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 78
agtgcagcca aaccagaaga aagccatgtt    30

<210> SEQ ID NO 79
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 79
agtgcagcca ttatatagga ctaac    25

<210> SEQ ID NO 80
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 80
agtgcagcca aaccagaaga    20

<210> SEQ ID NO 81
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 81
gtcgttcctg tggttaggac agggtcgcaa    30

<210> SEQ ID NO 82
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 82
gtcgttcctg ctggtgtctc agatcgttcg    30

<210> SEQ ID NO 83
<211> LENGTH: 25
<212> TYPE: DNA
<213> ORGANISM: ARTIFICIAL SEQUENCE

```
<220> FEATURE:
<223> OTHER INFORMATION: SYNTHETIC DNA

<400> SEQUENCE: 83
gtcgttcctg tggttaggac agggt                                    25

<210> SEQ ID NO 84
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 84
gtcgttcctg ctggtgtctc agat                                     24

<210> SEQ ID NO 85
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 85
aacggcgaca taaaataagt tgttacatgt                               30

<210> SEQ ID NO 86
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 86
aacggcgaca gtggcatgct cgatgacgac                               30

<210> SEQ ID NO 87
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 87
aacggcgaca taaaataagt tg                                       22

<210> SEQ ID NO 88
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 88
aacggcgaca gtggcatgct cgatg                                    25

<210> SEQ ID NO 89
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 89
ggtgaacgct gtagttggaa tataagtata                               30
```

<210> SEQ ID NO 90
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 90
ggtgaacgct cagatttaaa tataattagt                                    30

<210> SEQ ID NO 91
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 91
ggtgaacgct gtagttggaa tata                                          24

<210> SEQ ID NO 92
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 92
ggtgaacgct cagatttaaa tataat                                        26

<210> SEQ ID NO 93
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 93
ccgcagttag atgcaccatt agaattgctt                                    30

<210> SEQ ID NO 94
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 94
ccgcagttag atcaagtggc aaggttccat                                    30

<210> SEQ ID NO 95
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 95
ccgcagttag atgcaccatt                                               20

<210> SEQ ID NO 96
<211> LENGTH: 20
<212> TYPE: DNA
<213> ORGANISM: ARTIFICIAL SEQUENCE
<220> FEATURE:
<223> OTHER INFORMATION: SYNTHETIC DNA

-continued

<400> SEQUENCE: 96
ccgcagttag atcaagtggc                                           20

<210> SEQ ID NO 97
<211> LENGTH: 40
<212> TYPE: DNA
<213> ORGANISM: ARTIFICIAL SEQUENCE
<220> FEATURE:
<223> OTHER INFORMATION: SYNTHETIC DNA

<400> SEQUENCE: 97
gtcgttcctg tggttaggac agggtcgcaa attcagtctt                     40

<210> SEQ ID NO 98
<211> LENGTH: 40
<212> TYPE: DNA
<213> ORGANISM: ARTIFICIAL SEQUENCE
<220> FEATURE:
<223> OTHER INFORMATION: SYNTHETIC DNA

<400> SEQUENCE: 98
gtcgttcctg ctggtgtctc agatcgttcg ggggcttgcg                     40

<210> SEQ ID NO 99
<211> LENGTH: 12
<212> TYPE: DNA
<213> ORGANISM: ARTIFICIAL SEQUENCE
<220> FEATURE:
<223> OTHER INFORMATION: SYNTHETIC DNA

<400> SEQUENCE: 99
gtcgttcctg tg                                                   12

<210> SEQ ID NO 100
<211> LENGTH: 12
<212> TYPE: DNA
<213> ORGANISM: ARTIFICIAL SEQUENCE
<220> FEATURE:
<223> OTHER INFORMATION: SYNTHETIC DNA

<400> SEQUENCE: 100
gtcgttcctg ct                                                   12